(12) United States Patent
Suckow et al.

(10) Patent No.: US 8,257,715 B1
(45) Date of Patent: Sep. 4, 2012

(54) TISSUE VACCINES AND USES THEREOF

(75) Inventors: Mark A. Suckow, Granger, IN (US); William R. Wolter, South Bend, IN (US); Morris Pollard, Mishawaka, IN (US)

(73) Assignee: University of Notre Dame, Notre Dame, IN (US)

( * ) Notice: Subject to any disclaimer, the term of this patent is extended or adjusted under 35 U.S.C. 154(b) by 689 days.

(21) Appl. No.: 11/209,766

(22) Filed: Aug. 24, 2005

Related U.S. Application Data

(60) Provisional application No. 60/604,458, filed on Aug. 26, 2004.

(51) Int. Cl.
*A61K 39/00* (2006.01)

(52) U.S. Cl. ..................................... 424/277.1

(58) Field of Classification Search .................. None
See application file for complete search history.

(56) References Cited

U.S. PATENT DOCUMENTS

| | | | |
|---|---|---|---|
| 2,172,903 A | 9/1939 | Charping |
| 3,346,401 A | 10/1967 | Barat et al. |
| 3,562,820 A | 2/1971 | Braun |
| 3,810,473 A | 5/1974 | Cruz, Jr. et al. |
| 4,502,159 A | 3/1985 | Woodroof et al. |
| 4,578,067 A | 3/1986 | Cruz, Jr. et al. |
| 4,902,508 A | 2/1990 | Badylak et al. |
| 4,956,178 A | 9/1990 | Badylak et al. |
| 5,028,695 A | 7/1991 | Eckmayer et al. |
| 5,275,826 A | 1/1994 | Badylak et al. |
| 5,281,422 A | 1/1994 | Badylak et al. |
| 5,336,616 A | 8/1994 | Livesey et al. |
| 5,352,463 A | 10/1994 | Badylak et al. |
| 5,372,821 A | 12/1994 | Badylak et al. |
| 5,437,287 A | 8/1995 | Phillips et al. |
| 5,460,962 A | 10/1995 | Kemp |
| 5,480,424 A | 1/1996 | Cox |
| 5,507,810 A | 4/1996 | Prewett et al. |
| 5,554,389 A | 9/1996 | Badylak et al. |
| 5,695,998 A | 12/1997 | Badylak et al. |
| 5,733,337 A | 3/1998 | Carr, Jr. et al. |
| 5,782,914 A | 7/1998 | Schankereli |
| 5,837,269 A | 11/1998 | Daynes et al. |
| 6,120,991 A | 9/2000 | Carter et al. |
| 6,156,305 A | 12/2000 | Brauker et al. |
| 6,206,931 B1 | 3/2001 | Cook et al. |
| 6,207,147 B1 | 3/2001 | Hiserodt et al. |
| 6,218,166 B1 | 4/2001 | Ravindranath et al. |
| 6,227,368 B1 | 5/2001 | Truc |
| 6,264,992 B1 | 7/2001 | Voytik-Harbin et al. |
| 6,277,368 B1 | 8/2001 | Hiserodt et al. |
| 6,403,104 B1 | 6/2002 | Berd |
| 6,406,689 B1 | 6/2002 | Falkenberg et al. |
| 6,451,971 B1 | 9/2002 | Akiyama |
| 6,548,066 B1 | 4/2003 | Michaeli |
| 6,699,483 B1 | 3/2004 | Dalgleish et al. |
| 7,015,205 B1 | 3/2006 | Wallack |
| 7,090,853 B2 | 8/2006 | Kapp |
| 7,175,652 B2 | 2/2007 | Cook et al. |
| 7,550,004 B2 | 6/2009 | Bahler et al. |
| 2001/0006631 A1 | 7/2001 | Hiserodt et al. |
| 2002/0001595 A1 | 1/2002 | Sonntag et al. |
| 2004/0013712 A1 | 1/2004 | Parma |
| 2006/0099675 A1 | 5/2006 | Benard |
| 2006/0265053 A1 | 11/2006 | Hunt |
| 2007/0128174 A1 | 6/2007 | Kleinsek et al. |
| 2008/0107665 A1 | 5/2008 | Suckow et al. |
| 2008/0160049 A1 | 7/2008 | Suckow et al. |
| 2008/0254139 A1 | 10/2008 | Firestone |
| 2008/0260800 A1 | 10/2008 | Suckow et al. |
| 2009/0220461 A1 | 9/2009 | Suckow et al. |
| 2009/0248144 A1 | 10/2009 | Bahler et al. |
| 2010/0136050 A1 | 6/2010 | Suckow et al. |
| 2010/0233214 A1 | 9/2010 | Suckow et al. |
| 2011/0076305 A1 | 3/2011 | Suckow et al. |
| 2011/0135690 A1 | 6/2011 | Suckow |
| 2011/0150934 A1 | 6/2011 | Suckow |

FOREIGN PATENT DOCUMENTS

| | | |
|---|---|---|
| AU | 2007309193 | 5/2008 |
| AU | 2007345673 | 8/2008 |
| CA | 2667075 | 5/2008 |
| CA | 2627364 | 7/2008 |
| CN | 101730541 | 6/2010 |
| EP | 2109667 | 10/2009 |
| EP | 21144444 | 11/2009 |
| JP | 2010507584 | 3/2010 |

(Continued)

OTHER PUBLICATIONS

Ezzell, C. Cancer "vaccines": an idea whose time has come? The Journal of NIH Research, 1995. vol. 7, pp. 46-49.*

(Continued)

*Primary Examiner* — Anne M. Gussow
(74) *Attorney, Agent, or Firm* — Denise L. Mayfield

(57) ABSTRACT

Compositions comprising a tissue vaccine that include a mixture of heterogeneous tissue obtained from tumors and connective tissues. Vaccines comprising these compositions are also provided, as well as methods of using the vaccines in the treatment and/or inhibition of tumor growth, and particularly prostate tumor growth and cancers. The preparations may be defined as vaccines comprising tumor cells and connective (stromal) tissues derived from xenogeneic animals. Preparations comprising the tissue vaccines are provided using tissue harvested directly from tumors. Methods for preventing de novo development of cancer are also disclosed. A tissue vaccine comprising glutaraldehyde-(GFT) treated tissue prepared from tumor and connective tissue reduces the incidence of autochthonous prostate cancer. A tissue vaccine comprising a potassium thiocyanate extract (PTE) preparation of a tumor and connective tissue is also provided. The tissue vaccines are demonstrated to reduce the incidence of autochthonous prostate cancer.

41 Claims, 6 Drawing Sheets

FOREIGN PATENT DOCUMENTS

| JP | 2010516763 | 5/2010 |
|---|---|---|
| WO | WO97/36495 | 10/1997 |
| WO | WO03/100034 | 12/2003 |
| WO | 2008051852 | 5/2008 |
| WO | WO2008/051852 | 5/2008 |
| WO | 2008094276 | 8/2008 |
| WO | WO2008/094276 | 8/2008 |
| WO | 2008112344 | 9/2008 |
| WO | WO2008/112344 | 9/2008 |
| WO | WO2009/108656 | 9/2008 |
| WO | 2009108656 | 9/2009 |

OTHER PUBLICATIONS

Forni, G., Lollini, P.L., Musiani, P., and Colombo, M.P. Immunoprevention of Cancer. Cancer Research, 2000. vol. 60, pp. 2571-2575.*

Donnelly, J. Cancer vaccine targets leukemia. Nature Medicine, 2003. vol. 9 No. 11, pp. 1354-1356.*

Degruijl, T.D., and Curiel, D.T. Cancer vaccine strategies get bigger and bigger. Nature Medicine, 1999. vol. 5 No. 10, pp. 1124-1125.*

Bodey, B., Bodey Jr., B., Siegel, S.E., and Kaiser, H.E. Failure of cancer vaccines: the significant limitations of this approach to immunotherapy. Anticancer Research, 2000. vol. 20, pp. 2665-2676.*

Lee, Wang, Nielson, Wunderlich, Migueles, Connors, Steinberg, Rosenberg, and Marincola, Increased vaccine-specific T cell frequency after peptide-based vaccination correlates with increased susceptibility to in vitro stimulation but does not lead to tumor regression. Journal of Immunology, 1999. vol. 163, pp. 6292-6300.*

Chattergee, M.B., Foon, K.A., and Kohler, H. Idiotypic antibody immunotherapy of cancer. Cancer Immunology and Immunotherapy, 1994. vol. 38, pp. 75-82.*

Eaton, J.D., Perry, M.J.A., Nicholson, S., Guckian, M., Russell, N., Whelan, M., and Kirby, R.S. Allogeneic whole-cell vaccine: a phase I/II study in men with hormone-refractory prostate cancer. British Journal of Urology, 2002. vol. 89, pp. 19-26.*

Jarvinen, L.S., Hogenesch, H., Suckow, M.A., and Bowersock, T.L. Intranasal vaccination of New Zealand white rabbits against pasteurellosis, using alginate-encaspulated pasturella multocida toxin and potassium thiocyanate extract. Comparative Medicine, 2000. vol. 50 No. 3, pp. 263-269.*

Jager, E., Jager, D., and Knuth, A. Antigen-specific immunotherapy and cancer vaccines. International Journal of Cancer, 2003. vol. 106, pp. 817-820.*

Ben-Efraim, S., Bizzini, B., and Relyveld, E.H. Use of xenogenized (modified) tumor cells for treatment in experimental tumor and in human neoplasia. Biomed & Pharmacotherapy, 2000. vol. 54, pp. 268-273.*

Singh, S., Ross, S.R., Acena, M., Rowley, D.A., and Schreiber, H. Stroma is critical for preventing or permitting immunological destruction of antigenic cancer cells. Journal of Experimental Medicine, 1992. vol. 175, pp. 139-146.*

Ochsenbein, A.F., Klenerman, P., Karrer, U., Ludewig, B., Pericin, M., Hengartner, H., and Zinkernagel, R.M. Immune surveillance against a solid tumor fails because of immunological ignorance. Proceedings of the National Academy of Sciences, 1999. vol. 96, pp. 2233-2238.*

Dols, Smith, Meijer, Fox, Hu, Walker, Rosenheim, Moudgil, Doran, Wood, Seligman, Alvord, Schoof, and Urba. Vaccination of women with metastatic breast cancer, using a costimulatory gene (CD80)-modified, HLA-A2-matched allogeneic, breast cancer cell line: clinical and immunological results. Human Gene Therapy, 2003. vol. 14, pp. 1117-1123.*

Dillman, Beutel, De Leon, and Nayak. Short-term tumor cell lines from breast cancer for use as autologous tumor cell vaccines in the treatment of breast cancer. Cancer Biotherapy and Radiopharmaceuticals, 2001. vol. 16, pp. 205-211.*

Suckow, Wolter, and Pollard. Prevention of de novo prostate cancer by immunization with tumor-derived vaccines. Cancer Immunology and Immunotherapy, 2005. vol. 54, pp. 571-576.*

Suckow, Rosen, Wolter, Sailes, Jeffrey, and Tenniswood. Prevention of human PC-346C prostate cancer growth in mice by a xenogeneic tissue vaccine. Cancer Immunology and Immunotherapy, 2007. vol. 56, pp. 1275-1283.*

Okaji, Tsuno, Kitayama, Saito, Takahashi, Kawai, Yazawa, Asakage, Hori, Watanabe, Shibata, Takahashi, and Nagawa. Vaccination with autologous endothelium inhibits angiogenesis and metastasis of colon cancer through autoimmunity. Cancer Science, 2004. vol. 95, pp. 85-90.*

Simons, Mikhak, Chang, De Marzo, Carducci, Lim, Weber, Baccala, Goemann, Clift, Ando, Levitsky, Cohen, Sanda, Mulligan, Partin, Carter, Piantadosi, Marshall, and Nelson. Induction of immunity to prostate cancer antigens. Cancer Research, 1999. vol. 59, pp. 5160-5168.*

TEiR and Voutilainen. Effects of intraperitoneally injected suspensions of roentgen irradiated and non-irradiated tumor tissue on the growth of homologous tissue. Acta Pathol. Microbiol. Scand. 1957. vol. 40, pp. 273-282.*

Tallberg and Tykka. Specific active immunotherapy in advanced renal cell carcinoma: a clinical longterm follow-up study. World Journal of Urology, 1986. vol. 3, pp. 234-244.*

International Search Report, mailed Jul. 22, 2009 in PCT/US 09/35062.

Sanderson et al., (1974), "The induction of tumour immunity in mice using glutaraldehyde-treated tumor cells," Nature, 248:690-691.

Abraham et al., (2000), "Evaluation of the Porcine Intestinal Collagen Layer as a Biomaterial," J. Biomed. Res., 29:442-452.

Aguzzi et al., (2006), "Pathogenesis of prion diseases: current status and future outlook," Microbiology, 4:765-775.

Akhurst, (2002), "TGF-B antagonists: why suppress a tumor suppressor?" J. Clin. Invest., 109:1533-1536.

Baars et al., (2000), "Skin tests predict survival after autologous tumor cell vaccination in metastatic melanoma: experience in 81 patients," Ann. Oncol., 11:965-970.

Badylak et al., (1989), "Small intestinal submucosa as a large diameter vascular graft in the dog," J. Surgical Res., 47:74-80.

Badylak et al., (1998), "Small intestinal submucosa: a substrate for in vitro cell growth," J. Biomater. Sci. Polymer Edn., 9:863-878.

Badylak et al., (2002), "The extracellular matrix as a scaffold for tissue reconstruction," Cell Devel. Biol., 13:377-383.

Badylak, (1993), "Small intestinal submucosa (SIS): a biomaterial conducive to smart tissue remodeling," Tissue Engineering: Current Perspectives, Bell(ed)., Birkhauser Publishers, Cambridge, MA, pp. 179-189.

Barr et al., (2006), "Co-stimulatory agonists as immunological adjuvants," Vaccine, 24:3399-3407.

Bello-DeOcampo et al., (2004), "TGF-B/Smad signaling in prostate cancer," Curr. Drug Targets, 4:197-207.

Benbow, (2001), "Oasis®: an innovative alternative dressing for chronic wounds," Brit. J. Nursing, 10:1489-1492.

Bendani et al., (2006), "Combined vaccination with idiotype-pulsed allogeneic dendritic cells and soluble protein idiotype for multiple myeloma patients relapsing after reduced-intensity conditioning allogeneic stem cell transplantation," Leukemia & Lymphoma, 41:29-37.

Berd et al., (1990), "Treatment of metastatic melanoma with an autologous tumor-cell vaccine: clinical and immunologic results in 64 patients," J. Clin. Oncol., 8:8158-1867.

Berd et al., (1997), "Autologous hapten-modified melanoma vaccine as post-surgical adjuvant after resection of nodal metastases," J. Clin. Oncol., 15:2359-2370.

Berraondo et al., (2007), "Eradication of large tumors in mice by a tritherapy targeting the innate, adaptive, and regulatory components of the immune system," Cancer Res., 67:8847-8855.

Bissell et al., (1987), "The influence of extracellular matrix on gene expression: is structure the message?" J. Cell Sci., Suppl 8:327-343.

Brewer, (2006), "(How) do aluminium adjuvants work?" Immunol Lett., 102:10-15.

Brown-Etris et al., (2002), "Part I: A new biomaterial derived from small intestine submucosa and developed into a wound-matrix device," Wounds, 14:150-166.

Burch et al., (2000), "Priming tissue-specific cellular immunity in a phase I trial of autologous dendritic cells for prostate cancer," *Clin. Cancer Res.*, 6:2175-2182.

Burch et al., (2004), "Immunotherapy (APC8015, Provenge) targeting prostatic acid phosphatase can induce durable remission of metastatic androgen-independent prostate cancer: a phase 2 trial," *Prostate*, 60:197-204.

Caughey et al., (2006), "Prions and their Partners in Crime," *Nature*, 443:803-810.

Chang et al., (2000), "Antigen-Specific Cancer Immunotherapy Using a GM-CSF secreting allogeneic tumor cell-based vaccine," *Int. J. Cancer*, 86:725-730.

Charles et al., (2000), "Antitumor efficacy of tumor-antigen-encoding recombinant poxvirus immunization in dunning rate prostate cancer: implications for clinical genetic vaccine development," *World J. Urol.*, 18:136-142.

Corman et al., (1998), "Recognition of prostate-specific antigenic peptide determinants by human CD4 and CD8 T cells," *Clin. Exp. Immunol.*, 114:166-172.

Correale et al., (1997), "In vitro generation of human cytotoxic T lymphocytes specific for peptides derived from prostate-specific antigen," *J. Natl. Cancer Inst. USA*, 89:293-300.

Culora et al., (1996), "Aluminium and injection site reactions," *J. Clin. Pathol.*, 49:844-847.

Denmeade et al., (2003), "Prostate specific antigen (PSA) does not affect growth of prostate cancer cells in vitro or prostate cancer xenografts in vivo," *Prostate*, 56:45-53.

Dillman et al., (1998), "Clinical experience with autologous tumor cell lines for patient-specific vaccine therapy in metastatic melanoma," *Cancer Biother. Radiopharm.*, 13:165-173.

Edwards et al., (2005), "Annual report to the nation on the status of cancer, 1975-2002, featuring population-based trends in cancer treatment," *J. Natl. Cancer Inst.*, 97:1407-27.

Evans et al., (1999), "Vaccine therapy for cancer—fact or fiction?" *Q. J. Med.*, 92:299-307.

Finn et al., (2002), "Prophylactic Cancer Vaccines," *Curr. Opin. Immunol.*, 14:172-177.

Fong et al., (2001), "Dendritic cell-based xenoantigen vaccination for prostate cancer immunotherapy," *J. Immunol.*, 167:7150-7156.

Frost et al., (1975), "Tumor immunoprophylaxis in mice using glutaraldehyde-treated syngenic tumor cells," *Cancer Res.*, 35:2646-2650.

Fuessel et al., (2006), "Vaccination with hormone-refractory prostate cancer patients with peptide cocktail-loaded dendritic cells: results of phase I clinical trial," *Prostate*, 66:811-821.

Fukino et al., (2004), "Combined total genome loss of heterozygosity scan of breast cancer stroma and epithelium reveals multiplicity of stromal targets," *Cancer Res.*, 64:7231-6.

Furbert-Harris et al., (2003), "Inhibition of prostate cancer cell growth by activate eosinophils," *The Prostate*, 57:165-175.

Gann et al., (1999), "Lower prostate cancer risk in men with elevated plasma lycopene levels: results of a prospective analysis," *Cancer Research*, 59:1225-1230.

Gann et al., (1999), "Lower prostate cancer risk in men with elevated plasma lycopene levels: results of a prospective analysis," *JAMA*, 281:1682.

Glenn et al., (2006), "Mass vaccination: solutions 268. in the skin," *Curr. Topics Microbiol. Immunol.*, 304:247-268.

Granziero et al., (1999), "Adoptive immunotherapy prevents prostate cancer in a transgenic animal model," *Eur. J. Immunol.*, 29:1127-1138.

Greenlee et al., (2001), "Cancer Statistics 2001," *CA Cancer J. Clin.*, 51:15-36.

Griffith et al., (2001), "Inhibition of murine prostate tumor growth and activation of immunoregulatory cells with recombinant canarypox viruses," *J. Natl. Cancer Inst.*, 93:998-1007.

Gu et al., (2002), "Substitution of porcine small intestinal submucosa for rabbit Achilles tendon, an experimental study," *Natl. Med. J. China*, 82:1279-1282 (Chinese language with English abstract).

Gulley et al., (2002), "Phase I study of a vaccine using recombinant vaccinia virus expressing PAS (rV-PSA) in patients with metastatic androgen-independent prostate cancer," *The Prostate*, 53:109-117.

Hahn et al., (2006), "Short-term dietary administration of celecoxib enhances the efficacy of tumor lysate-pulsed dendritic cell vaccines in treating murine breast cancer," *Int. J. Cancer*, 118:2220-2231.

Harada et al., (2003), "Prostate-specific antigen-derived epitopes capable of inducing cellular humoral responses in HLA-A24+ prostate cancer patients," *Prostate*, 57:152-159.

He et al., (2003), "Inhibition of tumor growth with a vaccine based on xenogeneic homologous fibroblast growth factor receptor-1 in mice," *J. Biol. Chem.*, 24:21831-21836.

He et al., (2005), "Antigen epitope-expressing cytokines for DNA immunization," *Vaccine*, 23:1966-1972.

Higaki et al., (2004), "Collagen minipellet as a controlled release delivery system for tetanus and diphtheria toxoid," *Vaccine*, 19:3091-3096.

Hodde et al., (2002), "Virus safety of a porcine-derived medical device: evaluation of a viral inactivation method," *Biotechnol. Bioeng.*, 79:211-216.

Hodde et al., (2004), "Small Intestinal Submucosa does not promote PAIII tumor growth in Lobund-Wistar rats," *J. Surg. Res.*, 120:189-194.

Hodge et al., (2006), "Costimulatory molecules as adjuvants for immunotherapy," *Front. Biosci.*, 11:788-803.

Horiguchi et al., (2002), "Screening of HLA-A24-restricted epitope peptides from prostate-specific membrane antigen that induces specific antitumor cytotoxic T lymphocytes," *Clin. Cancer Res.*, 8:3885-3892.

Hrouda et al, (1998), "*Mycobacterium vaccae* (SRL172): a potential immunological adjuvant elevated in rate prostate cancer," 82:870-876.

Hrouda et al., (2000), "Allogeneic whole-tumor cell vaccination in the rat model of prostate cancer," *BJU International*, 86:742-748.

Huang et al., (2005), "A differential proteome in tumors suppressed by an adenovirus-based skin patch vaccine encoding human carcinoembryonic antigen," *Proteomics*, 5:1013-1023.

Hursting et al., (1990), "Types of dietary fat and the incidence of cancer at five sites," *Preventive Medicine*, 19:242-253.

Jocham et al., (2004), "Adjuvant autologous renal tumour cell vaccine and risk of tumour progression in patients with renal-cell carcinoma after radical neprectomy: phase III, randomised controlled trial," *Lancet*, 363:594-599.

Kenney et al., (2004), "Induction of protective immunity against lethal anthrax challenge with a patch," *J. Infect. Disease*, 190:774-782.

Knoll, (2001), "Use of porcine small intestinal submucosal graft in the surgical management of personae's disease," *Urology*, 57:753-757.

Knoll, (2002), "Use of porcine small intestinal submucosal graft in the surgical management of tunical deficiencies with penile prosthetic surgery," *Urology*, 59:758-761.

Kobayashi et al., (2003), "Identification of naturally processed helper T-cell epitopes from prostate-specific membrane antigen using peptide-based in vitro stimulation," *Clin. Cancer Res.*, 9:5386-5393.

Kochenderfer et al., (2007), "Maximizing CD8+ T cell responses elicited by peptide vaccines containing CpG oligodeoxynucleotides," *Clin. Immunol.*, 124:119-130.

Komenaka et al., (2004), "Immunotherapy for melanoma," *Clinics in Dermatology*, 22:251-265.

Lantz et al., (1990), "Small intestinal submucosa as a small-diameter arterial graft in the dog," *J. Invest. Surg.*, 3:217-227.

Lantz et al., (1993), "Small intestinal submucosa as a vascular graft: a review," *J. Invest. Surg.*, 6:297-310.

Li et al., (2008), "IL-21-mediated Foxp3 suppression leads to enhanced generation of antigen-specific CD8+ T lymphocytes," *Blood*, 111:229-235.

Lindblad, (2004), "Aluminium compound for use in vaccines," *Immunol. Cell Biol.*, 82:497-505.

Lord et al., (2007), "Low dose metronomic oral cyclophosphamide for hormone resistant prostate cancer: a phase II study," *J. Urology*, 177:2136-2140.

Lu et al., (2002), "Rcognition of prostate tumor cells by cytotoxic T lymphocytes specific for prostate-specific membrane antigen," *Cancer Res.*, 62:5807-5812.

Lubaroff et al., (2006), "Decreased cytotoxic T cell activity generated by co-administration of PSA vaccine and CpG ODN is associated with increased tumor protection in a mouse model of prostate cancer," *Vaccine*, 24:6155-6162.

Mantovani et al., (2003), "Reconstructive Urethroplasty using porcine acellular matrix," *Eur. Urol.*, 44:600-602.

Matrisian et al., (2001), "Epithelial-stromal interactions and tumor progression: meeting summary and future directions," *Cancer Res.*, 61:3844-3846.

Matsueda et al., (2005), "Identification of peptide vaccine candidates for prostate cancer patients with HLS-A3 super-type alleles," *Clin. Cancer Res.*, 11:6933-6943.

McDevitt et al., (2003), "Transforming growth factor-B1 in a sterilized tissue derived from the pig small intestine submucosa," *J. Biomed. Mater. Res.*, 67A:637-640.

McNeel et al., (2001), "Identification of T helper epitopes from prostatic acid phosphatae," *Cancer Res.*, 61:5161-5167.

Miller et al., (2006), "The role of melatonin in immuno-enhancement: potential application in cancer," *Int. J. Exp. Path.*, 87:81-87.

Moody et al., (1994), "Interleukin-2 transfected prostate cancer cells generate a local antitumor effect in vivo," *Prostate*, 24:244-251.

Moschella et al., (2003), "Shifting gene expression profiles during ex vivo culture of renal tumor cells: implications for cancer immunotherapy," *Oncology Res.*, 14:133-145.

Mosolitis et al., (2005), "Towards therapeutic vaccines for colorectal carcinoma: a review of clinical trials," *Expert Rev. Vaccines*, 4:329-350.

Nomura et al., (2000), "Serum selenium and subsequence risk of prostate cancer," *Cancer Epidemiology, Biomarkers & Prevention*, 9:883-887.

O'Connor et al., (2001), "Successful repair of uretero-neobladder structure using porcine small intestine submucosa," *J. Urology*, 165:1995.

O'Connor et al., (2002), "Distal ureteral replacement with tubularized porcine small intestine submucosa," *Urology*, 60:697x-697xii.

O'Connor et al., (2002), "Novel modification of partial nephrectomy technique using porcine small intestine submucosa," *Urology*, 60:906-909.

Ou et al., (2008), "Enhancement of dendritic cell-tumor fusion vaccine potency by indoleamine-pyrrole 2,3-dioxygenase inhibitor, 1-MT," *J. Cancer Res. Clin Oncol.*, 134:525-533.

Paradiso et al., (2003), "Plaque surgery for Peyronie's disease: heterologous grafts," *Archivio Italiano di Urologia e Andrologia*, 75:116-118 (Italian language with English abstract).

Peters et al., (1979), "Preparation of immunotherapeutic autologous tumor cell vaccines from solid tumors," *Cancer Res.*, 39:1353-1360.

Petrovsky, (2006), "Novel human polysaccharide adjuvants with dual Th1 and Th2 potentiating activity," *Vaccine*, 24S2:S2/26-S2/29.

Pilla et al., (2006), "A phase II trial of vaccination with autologous, tumor-derived heat-shocked protein peptide complexes Gp96, in combination with GM-CSF and interferon-a in metastatic melanoma patients," *Cancer Immunol. Immunother.*, 55:958-968.

Pollard et al., (1975), "Transplantable metastasizing prostate adenocarcinomas in rats," *J. Natl. Cancer Inst.*, 54:643-649.

Pollard et al., (1986), "Production of autochthonous prostate cancer in Lobund-Wistar rats by treatments with N-Nitroso-N-methylurea and testosterone," *J. Natl. Cancer Inst.*, 77:583-587.

Pollard et al., (1987), "Autochthonous prostate cancer in Lobund-Wistar rats; a model system," *The Prostate*, 11:219-227.

Pollard et al., (2005), "Hormone-refractory prostate cancer in the Lobund-Wister rat," *Exp. Biol. Med.*, 230:520-526.

Pollard et al., (2006), "Dietary prevention of hormone refracetory prostate cancer in Lobund-Wistar rats: a review of studies in relevant animal model," Comp. Med., 56:461-467.

Rechsteiner et al., (2005), "Cutting edge: priming of CTL by transcutaneous peptide immunization with imiquimod," *J. Immunol.*, 174:2476-2480.

Redfern et al., (2006), "Phase II trial of idiotype vaccination in previously treated patients with indolent non-Hodgkin's lymphoma resulting in durable clinical responses," *J. Clin. Oncol.*, 24:3107-3112.

Ringler et al., (1985), "Protection of rabbits against experimental pasteurellosis by vaccination with a potassium thiocyanate extract of *pasteurella multocida*," *Infection & Immunity*, 49:498-504.

Rousseau et al., (2006), "Immunotherapy of high-risk acute leukemia with a recipient (autologous) vaccine expressing transgenic human CD40L and IL-2 after chemotherapy and allogeneic stem cell transplantation," *Blood*, 107:1332-1341.

Ruozi et al., (2007), "Intact collagen and atelocollagen sponges: Characterization and ESEM observation," *Mat. Sci. Eng.*, 27:802-810.

Schultz et al., (2002), "Porcine small intestine submucosa as a treatment for enterocutaneous fistulas," *J. Am. Coll. Surg.*, 194:541-543.

Simons et al., (2002), "Phase II trials of a GM-CSF genetransduced prostate cancer cell line vaccine (GVAX) in hormone refractory prostate cancer," *Proc. Am. Soc. Clin. Oncol.*, 21:183a (Abstract 729).

Simons et al., (2006), "Granulocyte-macrophage colony-stimulating factor—transduced allogeneic cancer cellular immunotherapy: the GVAX® vaccine for prostate cancer," *Urol. Oncol.*, 24:419-424.

Skountzou et al., (2006), "Transcutaneous immunization with inactivated influenza virus induces protective immune responses," *Vaccine*, 24:6110-6119.

Small et al., (2000), "Immunotherapy of hormone-refractory prostate cancer with antigen-loaded dendritic cells," *J. Clin. Oncol.*, 18:3894-3903.

Small et al., (2005), "Results of a placebo-controlled phase III trial of immunotherapy with APC8015 for patients with homrone refractory prostate cancer (HRPC)," *Proc. Am. Soc. Clin. Oncol.*, 23(16S):378S. (Abstract 4500).

Srinivasan et al., (2004), "Tumor antigens for cancer immunotherapy: therapeutic potential of xenogeneic DNA vaccines," *J. Translational Med.*, 2:1-12.

Stack et al., (1982), "Autologous X-irradiated tumor cells and percutaneous BCG in operable lung cancer," *Thorax*, 37:599-593.

Suckow et al., (1999), "Enhanced bone regeneration using porcine small intestinal submucosa," *J. Invest.Surg.*, 12:277-287.

Suckow et al., (2005), "Use of porcine renal capsule matrix as a full-thickness dermal wound-healing material in rats," *J. Wound Care*, 14:137-140.

Suckow et al., (2007), "Surgical Repair of Experimental Achilles Tenotomy with Porcine renal capsule material in a rat model," *J. Mater. Sci. Mater. Med.*, 18:1105-1110.

Tatenhorst et al., (2005), "Genes associates with fast glioma cell migration in vitro and in vivo," *Brain Pathol.*, 15:46-54.

Totterman et al., (2005), "The immunotherapy of prostate and bladder cancer," *B.J.U. Intl.*, 96:728-735.

Vermorken et al., (1999), "Active specific immunotherapy for stage II and stage III human colon cancer: a randomized trial," *Lancet*, 353:345-350.

Vieweg et al., (1994), "Immunotherapy of prostate cancer in the Dunning rate model: use of cytokine gene modified tumor vaccines," *Cancer Res.*, 54:1760-1765.

Voytik-Harbin et al., (1998), "Small intestinal submucosa: a tissue-derived extracellular matrix that promotes tissue-specific growth and differentiation of cells in vitro," 4:157-174.

Wei et al., (2006), "Dendritoma vaccination combined with low dose interleukin-2 in metastatic melanoma patients induced immunological and clinical responses," *Intl. J. Oncol.*, 28:585-593.

Weiser et al., (2003), "Single layered small intestinal submucosa in the repair of sever chordee and complicated hypospadias," *J. Urology*, 170:1593-1595.

Wilson et al., (1997), "Human prostate tumor angiogenesis in nude mice: metalloprotease and plasminogen activator activities during tumor growth and neovascularization of subcutaneously injected matrigel impregnated with human prostate tumor cells," *Anatomical Record*, 249:63-73.

Xue et al., (1997), "Induction of human cytotoxic T lymphocytes specific for prostate-specific antigen," *Prostate*, 30:73-78.

Zhang et al., (2003), "Dendritic cells transfected with interleukin-12 and pulsed with tumor extract inhibit growth of murine prostatic carcinoma in vivo," *Prostate*, 55:292-298.

Aguzzi et al., (2003), "Immune system and peripheral nerves in propagation of prions to CNS," *Br Med Bull.*, 2003;66:141-59.

Allman et al., (2001), "Xenogeneic extracellular matrix grafts elicit a TH2-restricted immune response," *Transplantation*, 71:1631-1640.

Arbel et al., (2003), "Generation of antibodies against prion protein in wild-type mice via helix 1 peptide immunization," J Neuroimmunol., 144(1-2):38-45.

Banzhoff et al., (2003), "A new MF59-adjuvanted influenza vaccine enhances the immune response in the elderly with chronic diseases: results from animmunogenicity meta-analysis," *Gerontology*, 49(3):177-84.

Brando et al., (2007), "Murine immune responses to liver-stage antigen 1 protein FMP011, a malaria vaccine candidate, delivered with adjuvant AS01B or AS02A," *Infect Immun.*, 75(2):838-45.

Caglar et al., (2005), "Effect of monophosphoryl lipid A on antibody response to diphtheria toxin and its subunits," *APMIS*, 113(4):256-63.

de Souza Matos et al., (2000), "Immunostimulatory effects of polar glycopeptidolipids of Mycobacterium chelonae for inactivated rabies vaccine," *Vaccine*, 18(20):2125-31.

Desai et al., (2000), "Immune response with biodegradable nanospheres and alum: studies in rabbits using *staphylococcal* enterotoxin B-toxoid," *J Microencapsul.*, 17(2):215-25.

Eldridge et al., (1991), "Biodegradable and biocompatible poly(DL-lactide-co-glycolide) microspheres as an adjuvant for *staphylococcal* enterotoxin B toxoid which enhances the level of toxin-neutralizing antibodies," *Infect Immun.*, 59(9):2978-86.

Enari et al., (2001), "Scrapie prion protein accumulation by scrapie-infected neuroblastoma cells abrogated by exposure to a prion protein antibody," *Proc Natl Acad Sci U S A*, 98(16):9295-9.

Flick-Smith et al., (2002), "Mucosal or parenteral administration of microsphere-associated *Bacillus anthracis* protective antigen protects against anthrax infection in mice," *Infect Immun.*, 70(4):2022-8.
Gilch et al., (2003), "Polyclonal anti-PrP auto-antibodies induced with dimeric PrP interfere efficiently with PrPSc propagation in prion-infected cells," *J Biol Chem.*, 278(20):18524-31.
Griffiths et al., (1997), "Liposomally-encapsulated ricin toxoid vaccine delivered intratracheally elicits a good immune response and protects against a lethal pulmonary dose of ricin toxin," *Vaccine*, 15(17-18):1933-9.
Hanan et al., (2001), "Antiaggregating antibody raised against human PrP 106-126 recognizes pathological and normal isoforms of the whole prion protein," *Cell Mol Neurobiol.*, 21(6):693-703.
Hanan et al., (2001), "Immunomodulation of the human prion peptide 106-126 aggregation," Biochem Biophys Res Commun., 280(1):115-20.
Hedlund et al., (2001), "Negligible adjuvant effect for antibody responses and frequent adverse events associated with IL-12 treatment in humans vaccinated with *pneumococcal polysaccharide,"* *Vaccine*, 20(12):164-9.
Higgins et al., (1996), "MF59 adjuvant enhances the immunogenicity of influenza vaccine in both young and old mice," *Vaccine*, 14(6):478-84.
Jaganathan et al., (2006), "Strong systemic and mucosal immune responses to surface-modified PLGA microspheres containing recombinant hepatitis B antigen administered intranasally," *Vaccine*, 24(19):4201-11.
Kende et al., (2006), "Enhancement of intranasal vaccination in mice with deglycosylated chain a ricin by LTR72, a novel mucosal adjuvant," *Vaccine*, 15;24(12):2213-21.
Kenney et al., (1999), "Protective immunity using recombinant human IL-12 and alum as adjuvants in a primate model of cutaneous leishmaniasis," J Immunol , 163(8):4481-8.
Koller et al., (2002), "Induction of antibodies against murine full-length prion protein in wild-type mice," *J Neuroimmunol.*, 132(1-2):113-6.
Langermans et al., (2005), "Effect of adjuvant on reactogenicity and long-term immunogenicity of the malaria Vaccine ICC-1132 in macaques," *Vaccine*, 23(41):4935-43.
Levesque et al., (2006), "Association between immunogenicity and adsorption of a recombinant *Streptococcus pneumoniae* vaccine antigen by an aluminum adjuvant," *Hum Vaccin.*, 2(2):74-7.
Martin, (1997), "Development of an adjuvant to enhance the immune response to influenza vaccine in the elderly," *Biologicals*, 25(2):209-131.
Mendez et al., (2003), "Coinjection with CpG-containing immunostimulatory oligodeoxynucleotides reduces the pathogenicity of a live vaccine against cutaneous Leishmaniasis but maintains its potency and durability," *Infect Immun.* 71(9):5121-9.
Mullen et al., (2006), "Enhancement of functional antibody responses to AMA1 -C1/Alhydrogel, a Plasmodium falciparum malaria vaccine, with CpG oligodeoxynucleotide," *Vaccine*, 24(14):2497-505.
Palese, (2006), "Making better influenza virus vaccines?" *Emerg Infect Dis.*, 12(1):61-5.
Peng et al., (2006), "Novel vaccines for the treatment of chronic HBV infection based on mycobacterial heat shock protein 70," Vaccin, 24(7):887-96.
Peretz et al., (2001), "Antibodies inhibit prion propagation and clear cell cultures of prion infectivity," *Nature*, 412(6848):739-43.
Petrik et al., (2007), "Aluminum adjuvant linked to Gulf War illness induces motor neuron death in mice," Neuromolecular Med., 9:83-100.
Pimenta et al., (2006), "Intranasal immunization with the cholera toxin B subunit-pneumococcal surface against antigen A fusion protein induces protection against colonization with *Streptococcus pneumoniae* and has negligible impact on the nasopharyngeal and oral microbiota of mice," *Infect Immun.*, 74(8):4939-44.
Polymenidou et al., (2004), "Humoral immune response to native eukaryotic prion protein correlates with anti-prion protection," *Proc Natl Acad Sci U S A*,101 Suppl 2:14670-6.
Qin et al., (2004), "CpG ODNn enhances immunization effects of hepatitis B vaccine in aged mice," Cell Mol Immunol , 1 (2): 148-52.
Rosado-Vallado et al., (2005), "Aluminium phosphate potentiates the efficacy of DNA vaccines against Leishmania mexicana," *Vaccine*, 23(46-47):5372-9.
Rosset et al., (2004), "Breaking immune tolerance to the prion protein using prion protein peptides plus oligodeoxynucleotide-CpG in mice," *J Immunol.*, 172(9):5168-74.
Sabirov et al., (2006), "Intranasal vaccination of neonatal mice with polysaccharide conjugate vaccine for protection against pneumococcal otitis media," *Vaccine*, 24(27-28):5584-92.
Schwarz et al., (2004), "Immunisation with a synthetic prion protein-derived peptide prolongs survival times of mice orally exposed to the scrapie agent," *Neurosci Lett.*, 350(3):187-9.
Segura-Velazquez et al., (2006), "A novel synthetic adjuvant effectively enhances the immunogenicity of the influenza vaccine," *Vaccine*, 24(8):1073-80.
Sen et al., (2006), "Immunization of aged mice with a pneumococcal conjugate vaccine combined with an unmethylated CpG-containing oligodeoxynucleotide restores defective immunoglobulin G antipolysaccharide responses and specific CD4+-T-cell priming to young adult levels," *Infect Immun.*, 74(4):2177-86.
Sigurdsson et al., (2002), "Immunization delays the onset of prion disease in mice," *Am J Pathol.*, 161(1):13-7.
Souan et al., (2001), "Modulation of proteinase-K Immunol resistant prion protein by prion peptide immunization," *Eur J Immunol.*, 31(8):2338-46.
Stewart et al., (2006), "Pre-clinical evaluation of new adjuvant formulations to improve the immunogenicity of the malaria vaccine RTS,S/AS02A," *Vaccine*, 24(42-43):6483-92.
Suckow et al., (2007), "Tissue vaccines for cancer," *Expert. Rev. Vacc.*, 6:925-937.
Suckow et al., (2008), "Use of an extracellular matrix material as a vaccine carrier and adjuvant," *Anticancer Res.*, 28(5A):2529-2534.
Sugai et al., (2005), "A CpG-containing oligodeoxynucleotide as an efficient adjuvant counterbalancing the Th1/Th2 immune response in diphtheria-tetanus-pertussis vaccine," *Vaccine*, 23(46-47):5450-6.
Süli et al., (2004), "Experimental squalene adjuvant. I. Preparation and testing of its effectiveness," Vaccine, 22(25-26):3464-9.
Sung et al., (2006), "HBV-ISS (Dynavax)," *Curr Opin Mol Ther.*, 8(2):150-5.
Theeten et al., (2005), "Effects of lowering the aluminium content of a dTpa vaccine on its immunogenicity and reactogenicity when given as a booster to adolescents," *Vaccine*, 10;23(12):1515-21.
Vitetta et al., (2006), "A pilot clinical trial of a recombinant ricin vaccine in normal humans," *Proc Natl Acad Sci U S A*, 103(7):2268-73.

Extended European Search Report for EP Application No. 07844465.0, dated Mar. 31, 2010.
International Search Report for International Application No. PCT/US07/081962, dated Apr. 17, 2008.
Written Opinion for International Application No. PCT/US07/081962, dated Apr. 17, 2008.
International Search Report for International Application No. PCT/US07/069727, dated Dec. 4, 2007.
Written Opinion for International Application No. PCT/US07/069727, dated Dec. 4, 2007.
International Search Report for International Application No. PCT/US09/35062, dated Jul. 22, 2009.
Written Opinion for International Application No. PCT/US09/35062, dated Jul. 22, 2009.
International Search Report for International Application No. PCT/US08/51877, dated Dec. 17, 2008.
Written Opinion for International Application No. PCT/US08/51877, dated Dec. 17, 2008.
Zhang, et al., "Physicochemical Properties of Collagen, Gelatin and Collagen Hydrolysate Derived from Bovine Limed Split Wastes," Journal of the Society of Leather Technologists and Chemists, received Sep. 2005, p. 23, vol. 90.
Davis, et al., "Regulation of Tissue Injury Responses by the Exposure of Matricryptic Sites within Extracellular Matrix Molecules," American Journal of Pathology, May 2000, pp. 1489-1498, vol. 156, No. 5.
Leikina, et al., "Type I Collagen in Thermally Unstable at Body Temperature," PNAS, Feb. 5, 2002, pp. 1314-1318; vol. 99, No. 3.
Hirota, et al., "Collagen of Chronically Inflamed Skin is Over-Modified and Upregulates Secretion of Matrix Metalloproteinase 2 and Matrix-Degrading Enzymes by Endothelial Cells and Fibroblasts," The Journal of Investigative Dermatology, Dec. 2003, pp. 1317-1325, vol. 121, No. 6.
German Office Action dated Jun. 28, 2011.
S. Avrameas, et al., "Biologically Active Water-Insoluble Protein Polymers", The Journal of Biological Chemistry, vol. 242, No. 7, 1967, pp. 1651-1659.
Boring, CC et al., "Cancer Statistics," CA Cancer Journal for Clinicians, 1993, vol. 43, pp. 7-26.
Nomura, Abraham et al., "Serum Selenium and Subsequent Risk of Prostate Cancer," Cancer Epidemiology, Biomarkers & prevention, Sep. 2000, vol. 9, pp. 883-887.
Brooks, James D., et al., "Plasma Selenlum Level Before Diagnosis and the Risk of Prostate Cancer Development," Journal of Urology, Dec. 2001, vol. 166, pp. 2034-3038.
Hursting, Steven D., et al., "Types of Dietary Fat and the Incidence of Cancer at Five Sites," Preventive Medicine, (1990), vol. 19, pp. 242-253.
Gann, Peter H., et al., "Lower Prostate cancer Risk in Men with Elevated Plasma Lycopene levels: results of a Prospective Analysis," JAMA, May 12, 2999, vol. 281, No. 18, p. 1682, 1999.
Gann, Peter et al. "Lower Prostate Cancer Risk in men with Elevated Plasma Lycopene Levels: results of a Prospective Analysis," Cancer Research, Mar. 15, 1999, vol. 59, pp. 1225-1230.
Tjoe, B.A. et al., "Follow-Up Evaluation of a Phase II Prostate Cancer vaccine Trail," The Prostate, (1999) vol. 40, pp. 125-129.
Tjoe, Benjamin A. et al., "development of a Dendritic-Cell Based Prostate Cancer vaccine," Immunology Letters, (2000), vol. 74, pp. 873-893.
Gulley, James et al., "Phase I Study of a Vaccine Using recombinant Vaccinia Virus Expressing PSA (rV-PSA) in Pateints with Metastatic Androgen-Independent Prostate Cancer," The Prostate, (2002), vol. 53, pp. 109-117.
Pollard, Morris & Luckert, Phyllis, "transplantable Metastasizing Prostate Adenocarcinomas in Rats," Journal of the National Cancer Institute, Mar. 1975, vol. 54, No. 3, pp. 643-649.
Suckow, Mark et al., "Heat-Labile Toxin-Producing isolates of *Pasteurella multocida* From Rabbits," Laboratory Animal Science, Apr. 1991, vol. 41, No. 2, pp. 151-156.

Ringler, Daniel et al., "Protection of Rabbits against Experimental *Pasteurellosis* by Vaccination with a potassium Thlocyanate Exact of *Pasteurella multocida*," Infection and Immunity, Sep. 1985, vol. 49, No. 3, pp. 498-504.
Pollard, Morris & Luckert, Phyllis, "Production of Autochthonous Prostate Cancer in Lobund-Wistar rats by Treatments with N-Ntroso-N-methylurea and Testosterone," JNCI, Aug. 1986, vol. 77, No. 2, pp. 583-587.
Pollard, Morris & Luckert, Phyllis, "Autochthonous Prostate Adenocarcinomas in Lobund-Wistar Rats; A Model System," The Prostate, (1987), vol. 11, pp. 219-227.
Pollard, Morris, "Lobound-Wistar Rat Model of Prostate Cancer in Man," The Prostate, (1998), vol. 37, pp. 1-4.
Hrouda, D. et al., "*Mycobacterium vaccae* (SRL172): a Potential Immunological Adjuvant Elevated in Rat Prostate Cancer," British Journal of Urology, (1998), vol. 82, pp. 870-876.
Hrouda, D. et al., "Allogeneic Whole-Tumor Cell Vaccination in the Rat Model of Prostate Cancer," BJU International, (2000), vol. 86, pp. 742-748.
Griffith, Thomas S. et al., "Inhibition of Murine Prostate Tumor Growth and Activation of Immunoregulatory Cells with Recombinant Canatypox Viruses," Journal of the National Cancer Institute, Jul. 4, 2001, vol. 93, No. 13, pp. 998-1007.
Charles, Linda G. et al., "Antitumor Efficacy of Tumor-Antigen-Encoding Recombinanl Poxvirus Immunization in Dunning Rat Prostate Cancer: Implications for Clinical Genetic Vaccine Development," World J. Urol., (2000), vol. 18, pp. 136-142.
Michael, Agniesla et al., "Delayed Disease Progression after Allogeneic Cell Vaccination in Hormone-Resistant Prostate Cancer and Correlation with Immunologic Variables," Clin. Cancer. Res., Jun. 15, 2005, vol. 11, No. 12, pp. 469-4478.
Wang, Z. et al., "Lack of HLA Class I Antigen Expression by Melanoma Cells SK-Mel-33 Caused by Reading a Frameshift in $\beta_2$, Microglobulin Messenger RNA," J. Clin. Invest., Feb. 1993, vol. 91, pp. 648-692.
Shekhar, Malathy et al., "Breast Stroma Plays a Dominant Regulatory Role in Breast Epithetial Growth and Differentiation: Implications for Tumor Development and Progression," Cancer Research, Feb. 15, 2001, vol. 61, pp. 1320-1326.
Cunha, Gerald R. et al., "Role of the Stromal Microenvironment in Carcinogenesis of the Prostate," Int. J. Cancer, (2003), vol. 107, pp. 1-10.
Wei, Yu-Quan, "Immunotherapy of Tumors with Vaccines based on Xenogeneic Homologous Molecules," Anti-cancer Drugs, (2002), vol. 13, pp. 119-235.
Fong, Lawrence et al., "Dendritic Cell-Based Xenoantigen Vaccination or Prostate Cancer Immunotherapy," The Journal of Immunology, (2001), vol. 167, pp. 7150-7156.
Srinivasan, Roopa et al., "Tumor Antigens for Cancer Immunotherapy: Therapeutic Potential of Xenogeneic DNA Vaccines," Journal of Translational Medicine, 2004, vol. 2, pp. 1-12.
Bergman, Phillip J. et al., "Long-Term Survivla of Dogs with Advanced Malignant Melanoma After DNA Vaccination with Xenogeneic Human Tyrosinase: A Phase I Trial," Clinical Cancer Research, Apr. 2003, vol. 9, pp. 1284-1290.
He, Qiu-ming et al., "Inhibition of Tumor Growth with a Vaccine based on Xenogenetic Homologous Fibroblast Growth Factor Receptor-1 in Mice," Journal of Biological Chemistry, Jun. 13, 2003, vol. 24, pp. 21831-21836.
Fernandez-Acenero, M.J. et al., "Prognostic Influence of Tumor-Associated Eosinophilic Infiltrate in Colorectal Carcinoma," Cancer, (2002) vol. 88, pp. 1544-1548.
Ohashi, Yusuke et al., "Significance of Tumor Associated Tissue Eosinophilia and Other Inflammatory Cell Infiltrate in Early Esophageal Squamous Cell Carcinoma," Anticancer Research, (2002), vol. 20, pp. 3025-33030.
Furbert-Harris, Paulette et al., "Inhibition of Prostate Cancer Cell Growth by Activated Eosinophils," The Prostate, (2003), vol. 57, pp. 165-175.

* cited by examiner

TISSUE VACCINES AND USES THEREOF

CROSS REFERENCE TO RELATED APPLICATIONS

This application claims the benefit of U.S. Provisional application No. 60/604,458, filed Aug. 26, 2004, which is incorporated herein in its entirety.

BACKGROUND

1. Field of the Invention

The present invention relates generally to the field of vaccines, and more particularly to antitumor and anticancer vaccines. The invention also relates to the field of methods of treating and inhibiting tumor growth, particularly prostate tumor growth and cancer.

2. Related Art

Prostate cancer is a significant cause of cancer mortality in the western world.[1] Because current methods of treatment have shown only limited success in advanced cases, methods to reduce the incidence of disease would yield clear, significant benefit. Previous methods to prevent prostate cancer have focused primarily on dietary factors such as selenium[2, 19], dietary fat[4], and lycopene[5,6].

Though some potential benefit of vaccination has been demonstrated for treatment of individuals already having the disease[7,8,9], little work has been done to examine the possibility of preventing prostate cancer through vaccination.

U.S. Pat. No. 6,406,689 (Falkenberg et al.)[21] relates to the use of irradiated tumor cells for the prevention and treatment of various cancers, the vaccines therein having been prepared from established cell lines grown in vitro. Hrouda, et al. relates to the immunization of rats with a whole tumor cell vaccine and a non-specific adjuvant.[16,17] A recombinant poxvirus encoding tumor-associated antigens has also been described that was reported to protect rats against transplanted Dunning AT-2 prostate cancer cells.[19] A mixture of cultured allogeneic human prostate cancer cell lines which were inactivated by irradiation were used to extend the median time to disease progression in patients with high PSA values.[20]

These and other described vaccines were derived from single antigens or monoclonal cell cultures, and therefore when administered to an animal, offer limited antigenic challenge, and hence immunity to the animal. Because tumors exist in vivo in an environment composed of multiple cell and tissue types, a need continues to exist in the art for preparations that include a more representative composite of tumor and supportive tissue antigenic species. A need continues to exist in the medical arts for more effective treatments to halt and prevent cancer and tumor growth.

SUMMARY

The present invention is directed to overcoming the above-mentioned and other challenges related to preparations useful in the treatment and prevention of cancer and tumor growth. Embodiments of the present invention are exemplified in a number of implementations and applications, some of which are summarized below.

In one aspect, compositions are provided that comprise a tissue preparation. In some embodiments, the tissue preparation is a tissue vaccine. In some embodiments, the tissue vaccine comprises tumor tissue and connective tissue (stroma).

In some embodiments, the tissue vaccine is described as a heterologous mixture of antigens characteristic of whole tumor tissue and connective (stromal) tissue. In particular embodiments, the tissue vaccine comprises tumor tissue and connective tissue (stroma) that has been processed with a chemical agent. For example, the tumor tissue and connective tissue (stroma) may be processed with glutaraldehyde (GFT), potassium thiocyanate (PTE), or a combination thereof. These embodiments of the tissue preparation may be described as a glutaraldehyde tissue vaccine (GFT) or a potassium thiocyanate extract (PTE) vaccine.

In another aspect, a xenogeneic vaccine is provided. In some embodiments, the xenogeneic vaccine comprises components derived from tumor tissue harvested from one species of animal to prevent or treat tumors in an animal of another species.

In another aspect, methods are provided comprising treating an animal with a tissue vaccine. In some embodiments, the method comprises treating an animal to inhibit tumor growth or to prevent tumor development. The method in some embodiments comprises providing an animal with an effective amount of the tissue vaccine as described herein.

In particular embodiments, a method is provided for specifically treating a tumor, particularly for preventing or inhibiting tumor growth. In some embodiments, the method provides for administering an effective amount of a composition comprising a tissue vaccine to an animal having a tumor. In some embodiments, the tissue vaccine comprises a tumor and connective (stromal) tissue preparation that has been processed and/or treated with potassium thiocyanate or a glutaraldehyde (GFT) vaccine. In some embodiments, this tissue vaccine is described as a potassium thiocyanate extract (PTE) or a glutaraldehyde (GFT) vaccine.

In yet another aspect, a method for inhibiting de novo tumor cell growth is provided. In some embodiments, the method provides for administering an effective amount of a tissue vaccine to an animal. In particular embodiments, the tissue vaccine is a tumor and connective (stromal) tissue preparation that has been processed and/or treated with glutaraldehyde. In some embodiments, this tissue vaccine is described as a GFT tissue vaccine.

In some aspects, methods are provided for treating and/or inhibiting particular types of cancers, such as those characterized as hormone-influenced cancers. By way of example, in some embodiments, the hormone-influenced cancer comprises prostate, breast, testicular, uterine, and/or ovarian cancers.

In yet another aspect, methods are provided comprising immunizing an animal against cancer. In some embodiments, the cancer is a hormone-influenced cancer, such as prostate, breast, testicular, uterine, and/or ovarian cancer or an adenocarcinoma such as prostate, breast and lung cancer. In particular embodiments, the methods comprise immunizing an animal in need thereof with an effective amount of a composition comprising a vaccine comprising a tissue-composite. The tissue vaccine in some embodiments comprises a heterogeneous tissue composition comprising a diverse combination of materials obtained from both tumor and connective (stromal) tissues.

In yet other aspects, methods for preparing a tissue vaccine are provided.

The following abbreviations and acronyms are used throughout the description of the present invention:

CFA—Complete Freund's adjuvant;
GFT—Glutaraldehyde-tissue preparation;
LW—Lobund-Wistar;
MEM=minimal essential medium;

MNU=methylnitrosourea;
PSV=prostate/seminal vesicle
PTE=Potassium thiocyanate extract;

BRIEF DESCRIPTION OF THE DRAWINGS

The invention will be described in conjunction with the accompanying drawings, in which.

DETAILED DESCRIPTION

Figure 1:
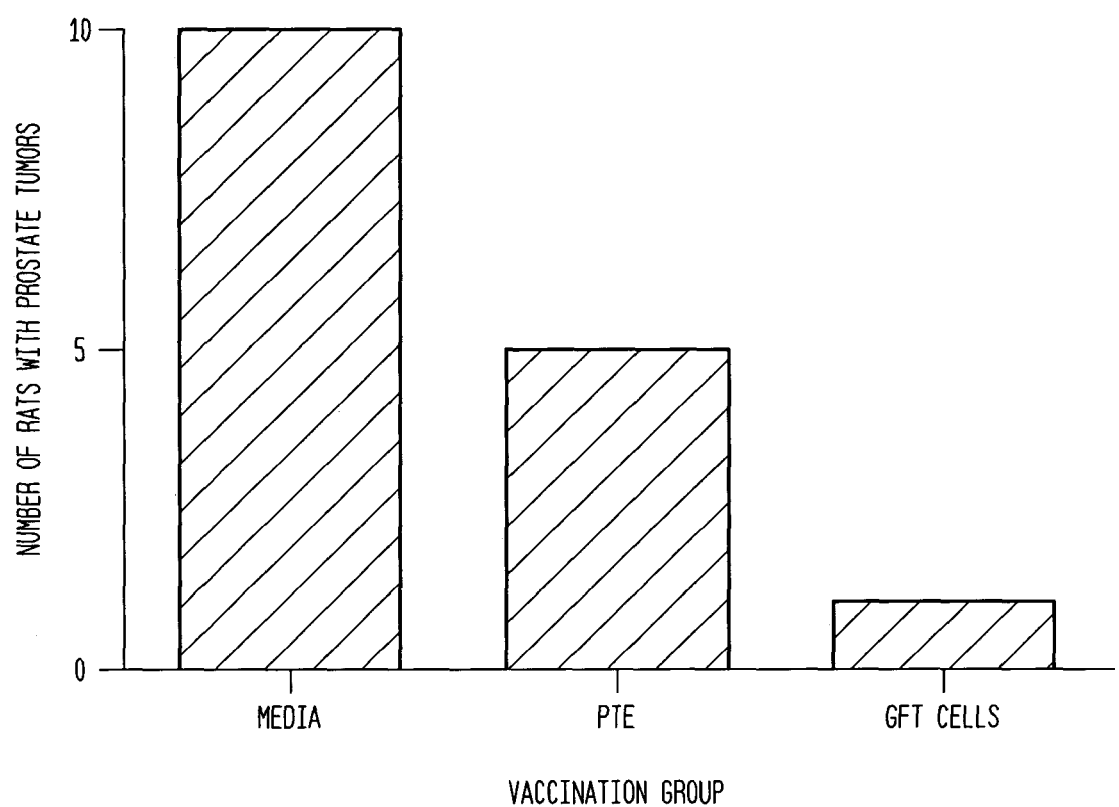
FIG. 1, in accordance with one embodiment of the invention, provides a graph showing the number of rats with de novo prostate tumors following vaccination with media, a potassium thiocyanate extract (PTE) of harvested tumor tissue, or glutaraldehyde-fixed tumor (GFT) cells.

It is advantageous to define several terms before describing the invention. It should be appreciated that the following definitions are used throughout this application.

DEFINITIONS

Where the definition of terms departs from the commonly used meaning of the term, applicant intends to utilize the definitions provided below, unless specifically indicated.

The term "stroma" refers to a whole cell mixture comprising animal supportive or connective tissue characteristic of that tissue located in or around a tissue or organ, particularly that connective and/or supportive tissue located in or around a tumor tissue or whole tumor as found in vivo, i.e., in the body. The stromal preparations may not be characterized by a single type or species of cells or proteins. For example, they may be instead characterized by a mixture of diverse antigenic species characteristic of a whole stromal tissue preparation as observed in vivo in association with a whole organ or tumor.

The term "tissue preparation" refers to a heterologous mixture of tumor cell and non-tumor cell tissue. The non-tumor cell tissue may comprise, for example, connective tissue, stroma, blood, serum, bone cells, blood, vessels, or any other animal cell other than tumor cells. The tissue preparation comprises a diverse mixture of defined and undefined antigenic species, and is comprised of antigens present on the surface and inside of whole tumor and associated (connective tissue) non-tumor cells, in a disrupted or intact cell form. A tissue vaccine of the present invention may include whole cells, cell lysates, tissue preparations that include tumor tissue and other tissues, such as connective and supporting tissues (stroma), etc. The term is not intended to be defined as an isolated cellular component or protein, or finite number of strictly enumerated antigenic species characteristic of a tumor cell or a connective tissue alone. Hence, as used herein, the tissue preparation and vaccines prepared there from or method employing them presents numerous targets (antigenic species) that induce an immunogenic response to a multiplicity of tumor tissue and connective tissue antigenic species. A broad spectrum antigenic immune response may thus be elicited in an animal vaccinated with the preparations, and may provide the anti-tumor activity described herein.

The term "tumor" refers to a combination of neoplastic tissue and associated supporting stroma and connective tissue.

The term "vaccine" refers to a preparation that contains components (antigenic species) capable of stimulating an immune response in an animal.

The term "GFT vaccine" refers to a tissue preparation that comprises a combination of tissue and stromal antigenic species characteristic of a tumor tissue and associated connective tissue that has been processed with glutaraldyhyde and is capable of demonstrating the tumor inhibiting activity of the glutaraldyhe processed tissue preparations described herein.

The term "PTE vaccine" refers to a tissue preparation that possesses a combination of tissue and stromal antigenic species characteristic of a tumor tissue and connective tissue that has been processed with potassium thiocyanate and is capable of demonstrating the tumor cell inhibiting activity of the potassium thiocyanate processed preparations and extracts described herein.

The term "xenogeneic" refers to a tissue or other material that is obtained form a source that is distinct from another, such as not having been obtained from the same species of animal (human vs. rat), or same type of animal tissue (heart vs. lung).

DESCRIPTION

The presently described compositions and tissue preparations provide anti-cancer and anti-tumor vaccines that prevent and/or inhibit cancer and tumor growth in vivo.

The tissue preparations may be described as processed tissue preparations in which a heterologous mixture of tumor antigenic species characteristic of intact tumor tissue and surrounding connective and stromal tissue has been preserved. In some embodiments, the processed tissue preparation comprises a whole tumor tissue and connective (stromal)

tissue sample that has been treated with glutaraldehyde- (GFT) or potassium thiocyanate (PTE).

Various embodiments of the tissue preparations comprise cells and tissues harvested directly from and/or surrounding a tumor as it exists in vivo. These tissue preparations have been found to prevent the development of and growth of cancer and tumors. The tissue preparations and vaccines comprise a mixed population of neoplastic cells and supporting connective tissues. The tissue preparations are thus composed of many antigenically different proteins. Furthermore, embodiments of the present invention do not use specific cancer cells, but rather tumor tissue (harvested after in vivo growth) comprised of multiple cell types (neoplastic cells, connective tissue, etc.). In addition, the tissue preparations and vaccines comprise tumor and connective (stomal) tissue antigenic species that are expressed in vivo.

Other embodiments of the invention will be apparent to those of skill in the art from consideration for the specification and practice of the invention disclosed herein. It is intended that the specification and examples be considered as exemplary only. The true scope and spirit of the invention may better be appreciated as set forth in the claims.

EXAMPLE 1

Materials and Methods

The present example sets forth the materials and methods employed in some of the embodiments of the invention, and as used throughout the description of the present invention.
Vaccine Preparations.

Two vaccine preparations were evaluated. Vaccine GFT was a glutaraldehyde-fixed tumor (GFT) suspension of cells harvested from tumors grown in animals. Vaccine PTE was a potassium thiocyanate extract (PTE) of harvested tumor tissue. Both Vaccine GFT and vaccine PTE were prepared from tumor tissue. Specifically, three grams of a subcutaneous tumor tissue was harvested from a Lobund-Wistar rat and used in the vaccine preparation. The subcutaneous tumor had been produced by administering prostate adenocarcinoma cells isolated from an autochthonous, metastatic prostate adenocarcinoma in a LW rat (See Pollard M, Luckert P H (1975)[10]).

The tissue was finely minced, repeatedly aspirated with a 1 cc syringe, and an aliquot drawn with a 20-gauge needle to eliminate large aggregates to create a cell suspension in modified Eagle's medium (MEM). A portion of the cell suspension was incubated in 2.5% glutaraldehyde (v/v) at 37° C. for 120 minutes and then washed thoroughly with media to produce the GFT cell preparation. Another portion was incubated in 1M KSCN and processed following previously described methods to produce a lysate, PTE (See Suckow M A, et al. (1991)[11]; and Ringler D H, et al. (1985)[12]). The PTE was then concentrated to 1.0 mg/ml for use in vaccination.
Animals.

LW rats obtained from a breeding colony maintained at the University of Notre Dame were used for all studies. In this model, large autochthonous prostate tumors develop in approximately 30% of males following a single dose of methylnitrosourea (See Pollard M, Luckert P H. (1986)[13]; and Pollard M., Luckert, P H. (1987)[14]).
Testosterone Assay.

Sera were assayed for testosterone using a commercial RIA kit (DSL-4000; Diagnostic Systems Laboratories, Inc.; Webster, Tex.). The test protocol recommended by the company was followed. The assays were performed directly with untreated serum, and with a sensitivity of 0.18 ng of testosterone/ml serum.
Study Design.

Rats were vaccinated subcutaneously with a 50:50 mixture of the vaccine preparation with Freund's complete adjuvant for the first dose and incomplete Freund's adjuvant for all subsequent doses. Each dose consisted of $5 \times 10^6$ GFT cells (GFT Vaccine), 0.5 mg of PTE protein (PTE Vaccine); or media (Control). The doses were chosen empirically based upon experience with bacterial vaccines.
Statistical Analysis.

Results of tumor occurrence were compared between groups using the Chi-square test with two degrees of freedom. Differences were considered significant when $p \leq 0.05$. Results for serum testosterone analysis were compared with the Wilcoxon rank sum test with significance reached when $p \leq 0.05$.

EXAMPLE 2

Vaccination with Tumor Vaccine Prevents De Novo Tumors

The present example is presented to demonstrate the utility of the invention for the prevention of de novo human prostate cancer growth.

The present invention demonstrates that vaccination of LW rats with a GFT whole cell preparation reduced the incidence of autochthonous prostate cancer by 90%, and vaccination with a PTE preparation reduced the incidence by 50%. These results reflect the complex heterogeneity of tumors beyond individual tumor cell types or antigens. The vaccine preparations of the present invention included antigens contributed not only by neoplastic cells, but also by the extensive connective tissue matrix within and surrounding a tumor. These antigens represent powerful immunogens, the sum of which elicits a protective response to the development of prostate cancer. That serum testosterone or testicle weights were not different in vaccinated rats versus controls indicates that the protective response was not due to anti-androgen activity. Further, the normal histological appearance of prostate-seminal vesicle tissue from rats lacking grossly visible tumors suggests that the protective immune response was not directed against antigens predominant in normal tissue.

The above-described results demonstrate that autochthonous prostate cancer may be prevented by vaccination. Further, the results demonstrate that the spleen plays an important role in this response, suggesting that the protective mechanism may involve cell-mediated immunity.

In the present example, a Lobund-Wistar rat MNU-induction model was used to demonstrate that vaccination with preparations derived directly from tumor tissue stimulates protective immunity against development of autochthonous prostate cancer. This model replicates many aspects of the human disease, including development of androgen-independent, autochthonous tumors which are refractory to therapy (Pollard M. (1998)[15]).

For the long-term study to evaluate the ability of vaccination to prevent development of autochthonous prostate cancer, groups of 30 rats were vaccinated monthly beginning at three months of age and continuing through 12 months. The animals were vaccinated with a GFT vaccine, PTE vaccine, or media (control) vaccine.

At four months of age, rats were administered an intravenous dose (30 mg/kg) of MNU, a cancer causative agent (Ash Stevens, Detroit, Mich.). At 12 months of age, rats were euthanized, serum harvested and frozen at −20° C. for testosterone assay, and necropsied. The weights of testicles were noted, and prostate-seminal vesicle complexes were fixed in 10% neutral buffered formalin for later staining with H & E (haematoxylin and eosin) in preparation for histological evaluation Results from the long-term study are shown in FIG. 1. Of the control animals, about 34% (10/30) rats vaccinated with media, developed grossly visible autochthonous prostate tumors. In contrast, only about 16% (5/30) of the PTE-Vaccine treated rats, and only about 3% (1/30) GFT Vaccine treated rats developed tumors, significantly fewer than the media-vaccinated controls. Rats that did not have grossly visible tumors in the prostate-seminal vesicle complex did not have histological evidence of neoplasia.

Figure 2:
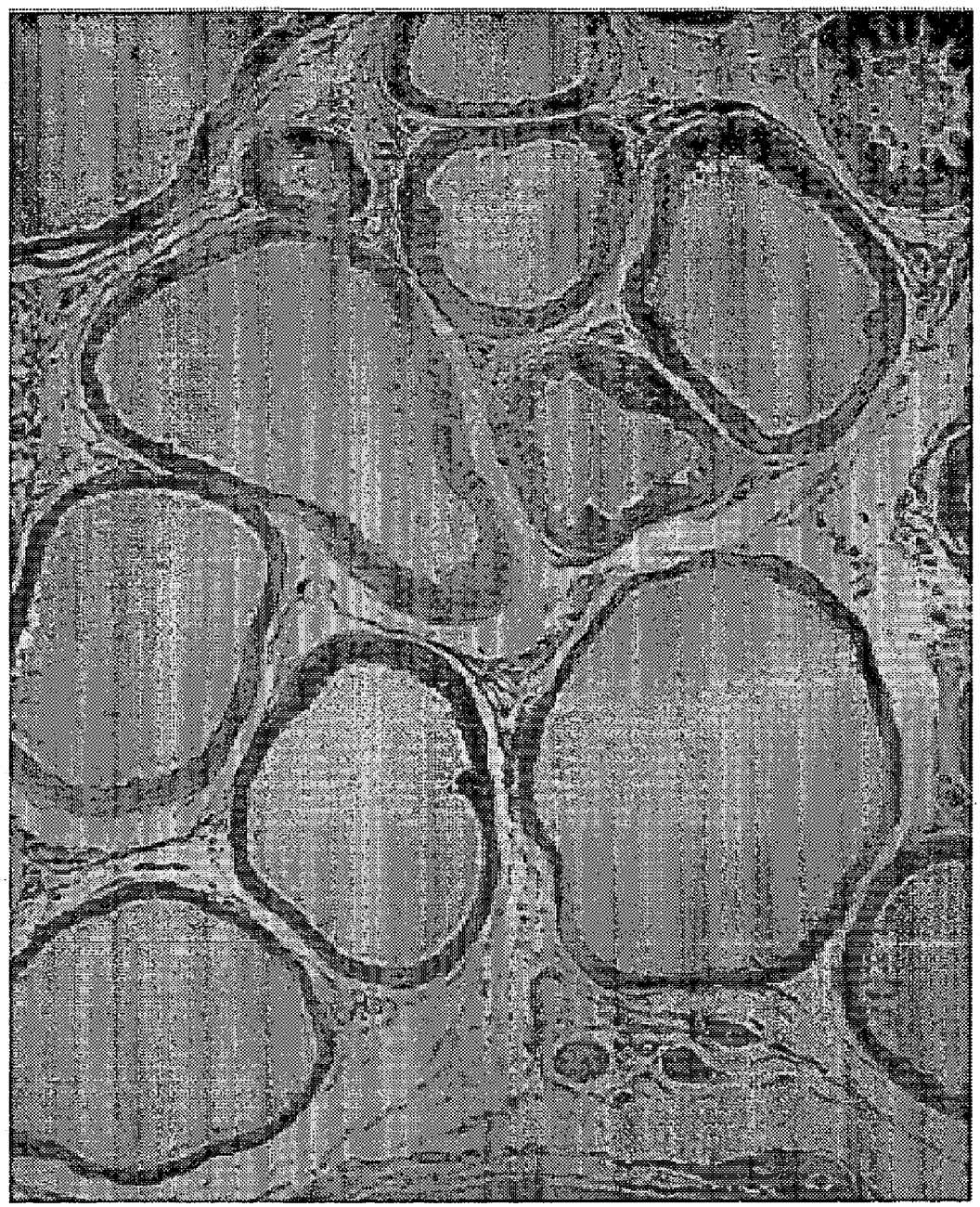
FIG. 2, in accordance with one embodiment of the invention, provides an image showing normal prostatic acini from a rat dosed once with methylnitrosourea and vaccinated monthly with GFT cells for 9 months. The section was stained with H & E and magnified 100×.

Further, prostate-seminal vesicle complexes from rats lacking grossly visible tumors showed normal histological features. No evidence of inflammation or atrophy was noted in prostates from any rats vaccinated with GFT or PTE vaccine, suggesting that the protective immunity was not directed against antigens predominant in normal tissue (FIG. 2).

Figure 3:
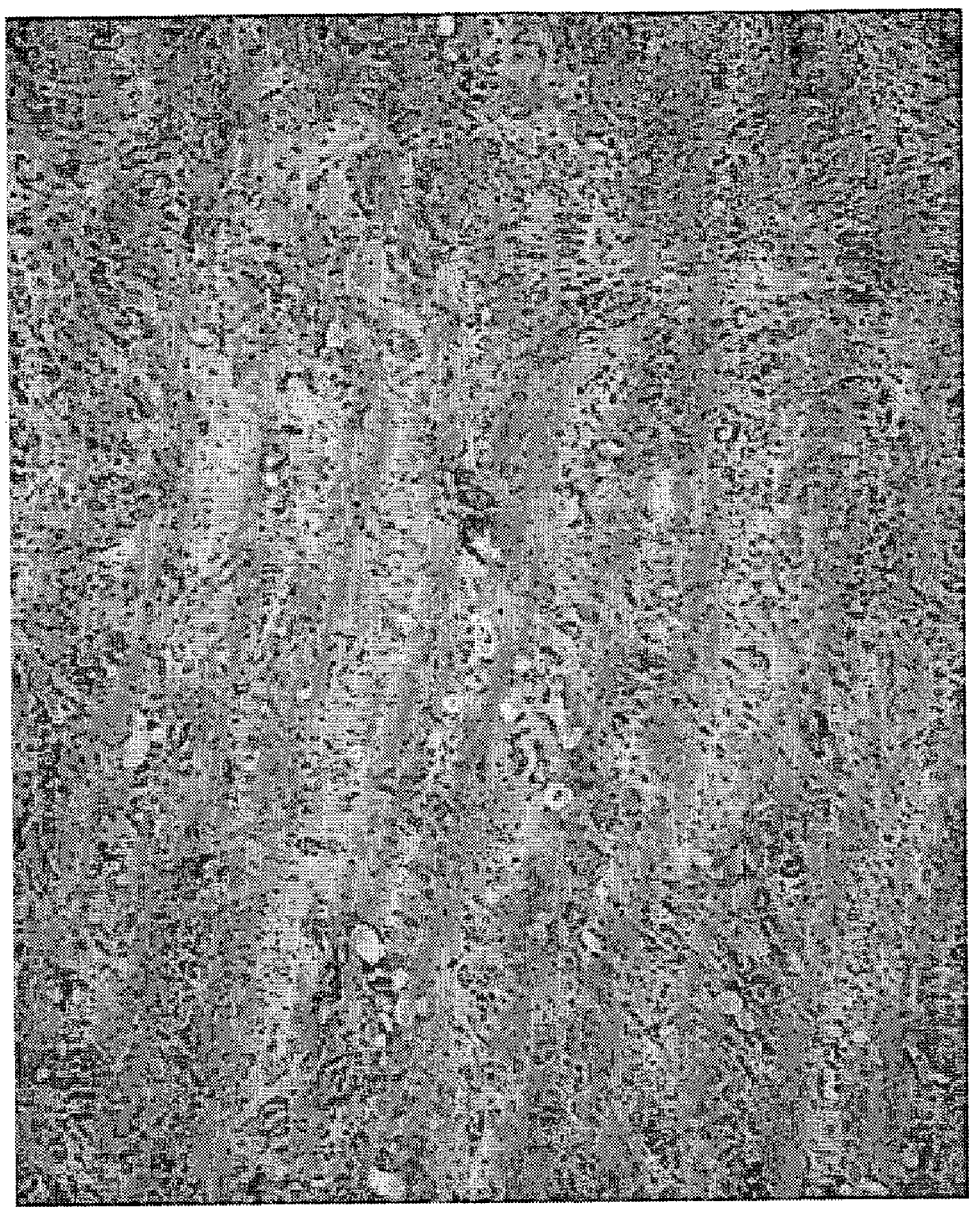
FIG. 3, in accordance with one embodiment of the invention, provides an image showing a section of an autochthonous prostate mass from a rat dosed once with methylnitrosourea and vaccinated monthly with media for 9 months. The section was stained with H & E and magnified 100×.

Tumors were adenocarcinomas, typical of those previously described in this model (FIG. 3) (See Pollard M (1998)[15]). There were no significant differences in serum testosterone concentrations at any individual time point or in the weights of testicles between any of the vaccination groups.

The inflammatory responses in tumors from GFT-vaccine treated rats and PTE-vaccine treated rats were distinguished by an influx of eosinophils compared to the responses in tumors from media-vaccinated rats.

The inflammatory response at the tumor margin was evaluated by enumerating mononuclear and granulocytic inflammatory cells over ten high-powered (40× objective) fields. The results are expressed as percentages of total inflammatory cells by cell type. Necrotic foci within tumors from all three groups were located distant to tumor margins and blood vessels, and included an influx of neutrophils. At the tumor margins, where the immune system might be expected to mount an active response to the expanding tumor, the inflammatory response in a Control vaccine treated animal was composed primarily of neutrophils (74%), lymphocytes (12%), and macrophages (14%). In contrast, the inflammatory response at the margin of a tumor from a GFT vaccine treated animal was composed of eosinophils (33%), neutrophils (27%), lymphoctes (22%) and macrophages (18%). In PTE-vaccinated rats, the inflammatory response at the tumor margin was composed of eosinophils (22%), neutrophils (29%), lymphocytes (28%), and macrophages (21%).

The marked tumor-associated tissue eosinophilia at the tumor margins of GFT-vaccinated and PTE-vaccinated rats distinguishes those inflammatory responses from that observed in tumors from media-vaccinated rats. Tumor-associated eosinophilic infiltrate has been shown to be a favorable prognostic indicator in colorectal carcinoma and early esophageal squamous cell carcinoma (See Fernandez-Acerno M J, et al. (2000)[30]; and Ohashi Y, et al. (2000)[31]). Activated eosinophils or their culture supernatants significantly inhibited the growth of the cultured human prostate cancer cells (Furbert-Harris P, et al. (2003)[32]). Large numbers of eosinophils were present at tumor margins in GFT Vaccine- and PTE-Vaccine treated rats. Both of these treated groups developed significantly fewer tumors than Control (media) Vaccine treated rats. A possible role for eosinophils in the protective immune response conferred by GFT cell and PTE vaccination may exist.

EXAMPLE 3

Tissue Vaccine for Treatment of Tumors

The present example demonstrates the utility of the invention to elicit protective immune response following a short term immunization regimen employing the tissue-vaccine preparations of the present invention.

To evaluate the role of the spleen in generating the protective immune response following vaccination, three (3) groups of ten (10) rats were vaccinated initially with one of three (3) vaccine treatments, GFT Vaccine, PTE Vaccine or Control (media) Vaccine, and boosted seven days later. Fourteen days after initial vaccination, rats were euthanized, spleens aseptically harvested and dissociated into MEM using a screen, and co-incubated for three hours at 37° C. with harvested tumor cells (1:1 ratio of splenocytes:tumor cells). The cell suspension was then administered subcutaneously into the flank of naive LW rats such that each rat received a volume containing $2 \times 10^6$ cells. Rats were euthanized 28 days later and the presence or absence of grossly observable tumors noted.

Figure 4:
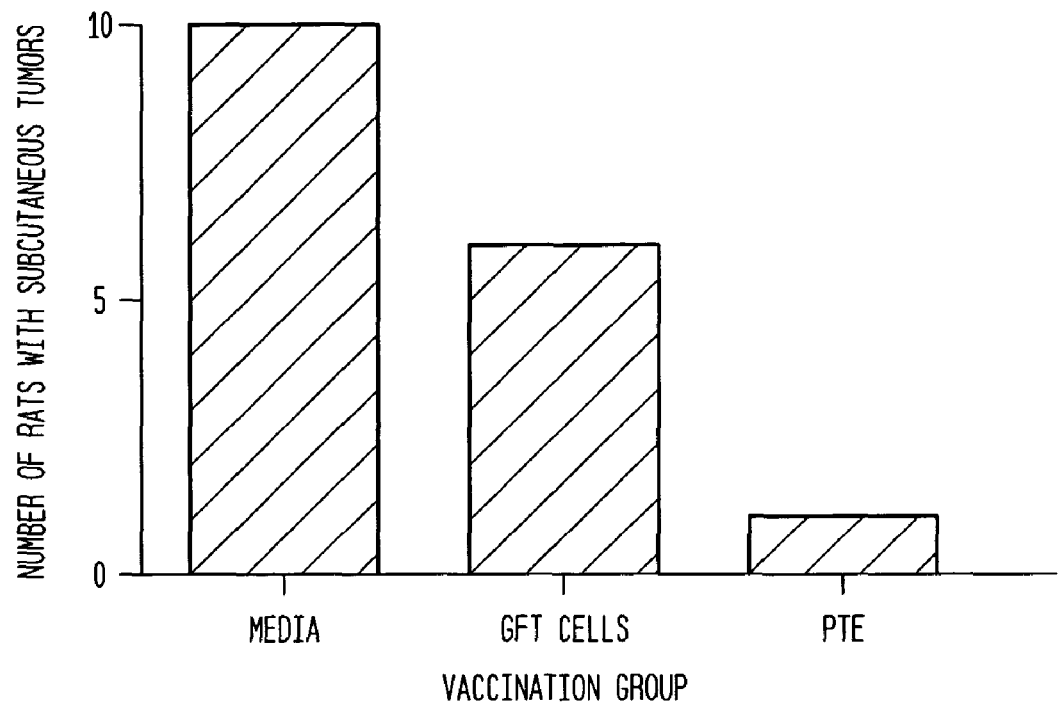
FIG. 4, in accordance with one embodiment of the invention, provides a graph showing the number of rats with subcutaneous tumors following administration of tumor cells which had been incubated with splenocytes from either media-vaccinated, GFT cell-vaccinated or PTE-vaccinated rats.

Results from the short-term vaccination study are shown in FIG. 4. All 10/10 (100%) of the rats administered a vaccine prepared from tumor cells co-incubated with splenocytes from Control (media)-vaccinated rats developed subcutaneous tumors. In contrast, only 60% (6/10) and 20% (2/10) of the animals administered a vaccine prepared from tumor cells co-incubated with splenocytes from GFT-vaccinated and PTE cell-vaccinated rats, respectively, developed tumors. Both of these groups had significantly fewer rats with tumors compared to rats receiving tumor cells which had been co-incubated with splenocytes from control (media)-vaccinated rats.

EXAMPLE 4

Repeated Vaccination with Tumor Tissue Vaccine Does Not Result in Autoimmune Disease The present example demonstrates that vaccination with the tumor tissue vaccines of the present invention does not result in the development of autoimmune disease.

Animals were subjected to repeated vaccinations of the tumor tissue vaccines and then examined for the existence of any histological evidence of autoimmune disease. Groups of 10 three-month-old LW rats were each immunized and boosted monthly for 12 months with MEM (control), PTE vaccine or GFT vaccine. Freund's complete adjuvant was used in the initial vaccination, and Freund's incomplete adjuvant was used in the booster vaccinations. Tissues were then harvested from the animals at 15 months of age, fixed in 10% neutral buffered formalin, sectioned at 3-4 μm and stained with hematoxylin and eosin. All rats were clinically normal for the duration of the study. Kidney, heart, brain, liver, testis, prostate/seminal vesicle, and spleen were examined and all found to be histologically normal.

The results demonstrate that repeated immunization with a tumor tissue vaccine, such as the PTE or GFT tumor tissue vaccine preparations, does not induce tissue damage related to autoimmunity.

EXAMPLE 5

The Protective Effect of Tumor Tissue Vaccination Does Not Result from Serum Antibody To determine if serum factors, such as antibody, are responsible for the protective effect associated with vaccination, two rats each vaccinated subcutaneous with MEM with adjuvant (Control vaccine); PTE processed tumor cells with adjuvant; or GFT processed tumor cells with adjuvant. Rats were boosted once, 7 days after initial vaccination. Freund's complete adjuvant was used in the initial vaccination, and Freund's incomplete adjuvant was used in the booster vaccination. Seven days after the booster vaccination, the rats were euthanized and serum harvested.

Tumor cells harvested from a subcutaneously passaged tumor were then incubated at a dilution of $8\times10^6$ cells per ml of harvested serum for 3 hours at 37° C. A volume of about 0.25 ml of this suspension (equivalent to about $2\times10^6$ cells) was administered subcutaneously in the flank of LW rats (6/group). Rats were then necropsied 3 weeks later and the number of animals bearing tumors was compared. The results (number having tumors/total number per group) were:

PTE rats=5/6
GFT cell rats=6/6
MEM rats=6/6

This study suggests that humoral antibody is not responsible for the protective immune response demonstrated in tumor tissue vaccine treated animals.

EXAMPLE 6

Vaccination with Tumor Tissue Vaccines Reduces the Size of Transplanted Tumors and Inhibits Metastasis from the Primary Tumor To determine if vaccination has a protective effect against metastasis from a primary tumor, groups of ten rats were vaccinated subcutaneously with media, GFT vaccine, or PTE vaccine and boosted weekly for two weeks. Freuend's complete adjuvant was used in the initial vaccination, and Fruend's incomplete adjuvant was used in booster vaccinations. At the time of the second boost, $2\times10^6$ cells harvested from a subcutaneously passaged LW prostate tumor were administered to each rat, subcutaneously. Six weeks later, the rats were euthanized. Weights of subcutaneous tumors were:

Media control=11.44 gm
PTE=9.15 gm
GFT cells=8.88 gm

Group differences were not significant ($P>0.05$) but there appears to be a trend toward reduced tumor size in vaccinated groups.

Figure 5:
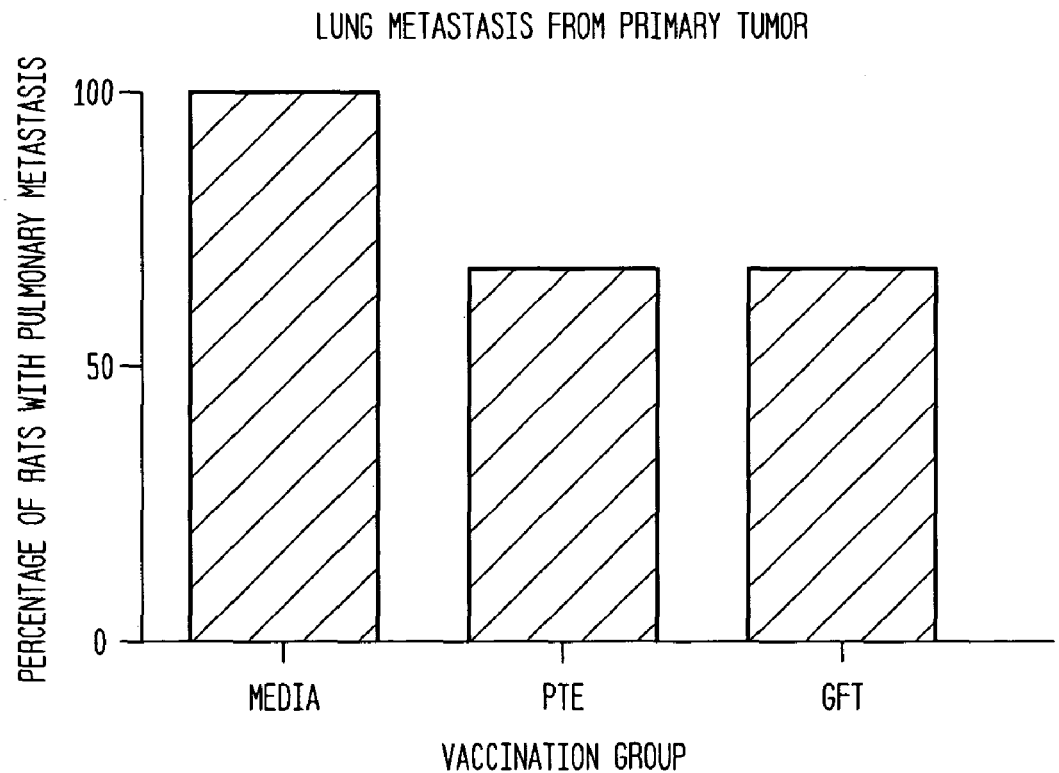
FIG. 5, in accordance with one embodiment of the invention, provides a graph showing the percentage of vaccinated rats with primary tumors having metastatic foci to the lungs.

For lung metastases, 100% (10/10) of the Control (Media) rats had metastatic foci in the lungs; 70% (7/10) of the PTE-tumor cell vaccinated rats had metastatic foci in the lungs; and 70% (7/10) of the GFT tumor cell-vaccinated rats had metastatic foci in the lungs. These results, depicted in FIG. 5, demonstrate that a protective effect was provided n the tumor cell vaccinated animals.

The results of this study demonstrate that vaccination with a vaccine that includes—tumor cells effectively reduces the size of existing tumors and inhibits metastasis from the primary tumor.

EXAMPLE 7

Vaccination with the Tumor Tissue Vaccine Reduces Growth of Metastatic Tumor Foci Following Resection of a Primary Tumor To evaluate the effect of vaccination on metastasis following resection (Res) of a primary tumor, subcutaneous tumors were produced in 3-month-old LW rats by administering $2\times10^6$ cells from a subcutaneously passaged prostate tumor harvested from a LW rat. The resulting subcutaneous tumors were surgically resected after 17 days in 33 rats. At the time of resection, 10 rats were immunized with GFT vaccine and adjuvant; 10 rats were immunized with MEM (control) plus adjuvant; 10 rats underwent resection but had no further treatment; and 3 rats did not undergo resection or vaccination. All vaccinated rats underwent booster vaccination weekly for 3 weeks. Initial vaccination included Freund's complete adjuvant, and booster vaccinations included Freund's incomplete adjuvant. Six weeks after resection, rats were euthanized and necropsied; the metastatic foci on the pleural surfaces of the lungs were counted and measured with a caliper.

Mean numbers of lung foci:
Resection only=20.40 gm (SD 5.2)
Res.+GFT=11.60 gm (SD 7.9)
Res.+media=22.67 gm (SD 7.2)
No resection=17.00 gm (SD 1.0)

There was no significant difference in the mean number of lung foci observed in rats which underwent resection followed by vaccination with GFT vaccine compared to animals which underwent resection only ($P<0.05$); and between rats which underwent resection followed by vaccination with GFT vaccine compared to animals which underwent resection followed by vaccination with control vaccine (media) ($P<0.01$).

Figure 6:
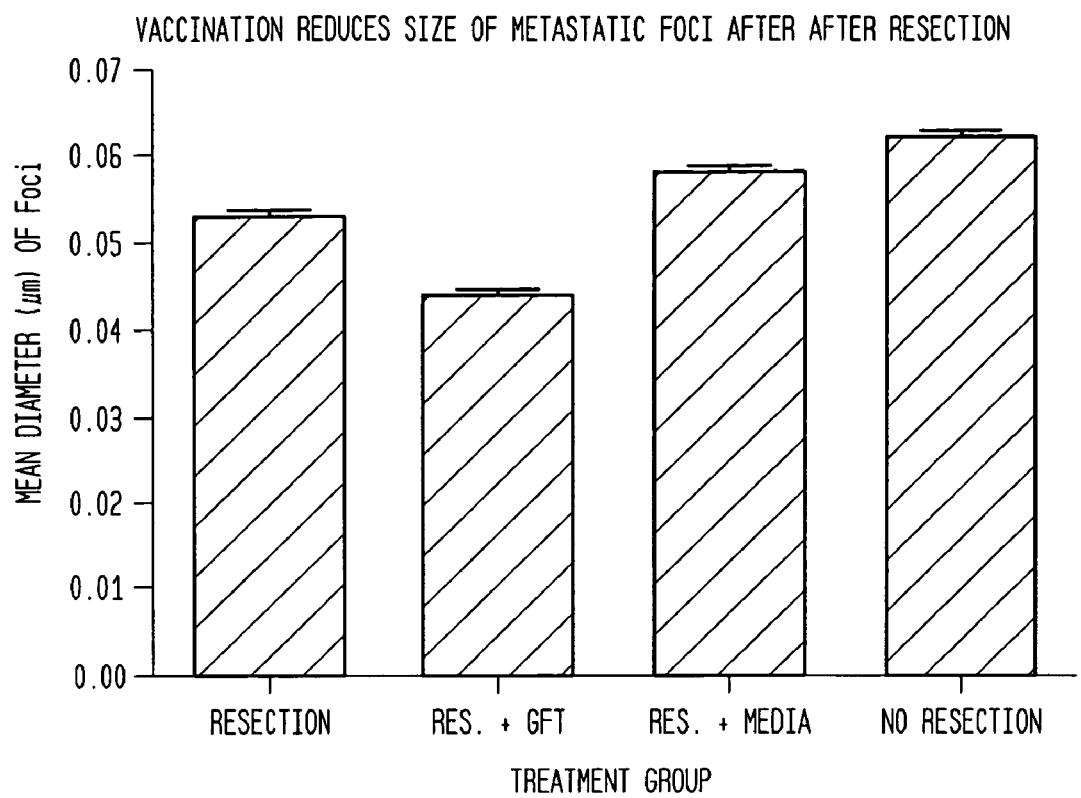
FIG. 6, in accordance with one embodiment of the invention, provides a graph showing the size of metastatic foci in the lungs following resection of the primary tumor and vaccination.

The mean diameter (µm) for lung foci are depicted in FIG. 6 and were:

Resection only=0.053 (SD 0.017)
Res.+GFT=0.046 (SD 0.018)
Res.+Media=0.058 (SD 0.020)
No resection=0.062 (0.023)

There is a significant difference in the mean diameter of metastatic foci observed in the lungs between rats undergoing resection only and rats undergoing resection followed by vaccination with GFT vaccine ($P<0.05$); between rats undergoing resection followed by vaccination with GFT vaccine and rats undergoing resection followed by vaccination with a control (media) vaccine ($P<0.001$); and between rats undergoing resection followed by vaccination with GFT vaccine and rats not undergoing resection (0.001). The significant reduction in size of metastatic foci in rats undergoing resection and GFT vaccination compared to all other groups indicates that growth of metastases are suppressed by GFT vaccination.

These results show that, while vaccination with GFT vaccine does not reduce the number of metastatic foci compared to resection alone, vaccination reduces the growth of metastatic foci.

EXAMPLE 8

Xenogeneic Vaccination with Non-Human Tumor Tissue Vaccine Stimulates Protective Immunity Against Human Cancer Cells Immunization with xenogeneic DNA is an attractive approach in the treatment of cancer because it generates T cell and antibody responses (Srinivasan and Wolchok (2004)[27]). In the present example, a xenogeneic tissue immunization model is set forth that demonstrates the utility of the present invention for providing xenogeneic tumor vaccines that protect against human cancer cell growth. In the present example, rat tumor tissue was used to prepare a tumor tissue vaccine. The data presented here demonstrates the efficacy of the tumor tissue vaccines for the prevention and treatment of cancer, particularly for prostate cancer.

Testosterone pellets (12.5 mg) were implanted subcutaneously into each of 30 athymic nude mice (NCR Balb/C). The testosterone was administered to prepare the in vivo environment for growth of transplanted human prostate cancer cells as described below.

Groups of five immunocompetent male (NCr)—Foxn1 <nu> (Tac) mice (8 weeks old) were immunized subcutaneously with either MEM (Control), a GFT vaccine ($1\times10^6$ GFT tumor cells), or left non-immunized. This is the background strain for the athymic nude mice described herein. The mice in each of these treatment groups were boosted weekly for 3 weeks. Freund's complete adjuvant was used in the initial vaccination, and Freund's incomplete adjuvant was used in booster vaccinations. One week after the final booster vaccination, mice were euthanized and their spleens and serum harvested. Spleens were aseptically harvested, dissociated, pooled for each group, and the red blood cells lysed with ammonium chloride solution. The remaining splenocytes were incubated in modified Eagles medium (MEM) for 3 hours at 37° C. with PC346 human prostate cancer cells (1:4 ratio of mouse splenocyte:PC346 human prostate cancer cells).

Nude mice were anesthetized and prepared for aseptic surgery. Ten mice per each vaccination group were implanted (via orthotopic administration into the prostate gland) with 40,000 PC346 human cancer cells+10,000 mouse splenocytes in Matrigel® (BD Biosciences®, Parsipanny, N.J.). Several animals died prior to scheduled harvest, with gross necropsy being non-diagnostic due to advanced autolysis. Eight weeks later, all remaining animals were euthanized and evaluated for the presence of prostate tumors. Prostate/seminal vesicle (PSV) weights were obtained, and tissue fixed in formalin. Fixed tissue was later sectioned at 3-4 µm and stained with hematoxylin and eosin.

Figure 7:
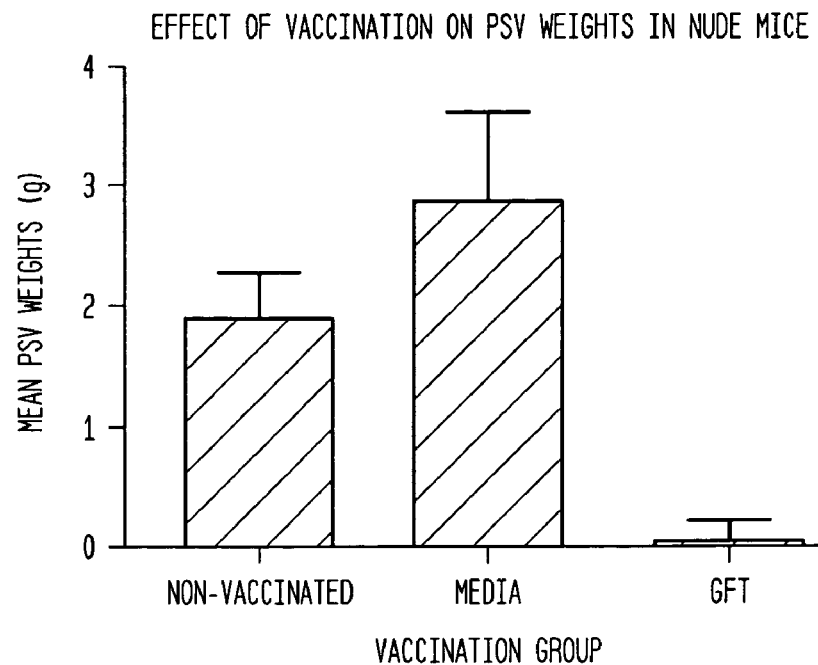
FIG. 7, in accordance with one embodiment of the invention, provides a graph showing the weights of prostate-seminal vesicle (PSV) complexes in nude mice transplanted with human PC346 prostate cancer cells which had been co-incubated with splenocytes from immunocompetent mice which were not vaccinated or which had been vaccinated with either media or GFT vaccine (of rat tissue origin FIG. 8, in accordance with one embodiment of the invention, provides a graph showing the percentage of nude mice with histological evidence of growth of transplanted human PC346 prostate cancer cells. These mice were transplanted orthotopically with PC346 cells which had been co-incubated with splenocytes from immunocompetent mice which were either not vaccinated or which had been vaccinated with either media or GFT vaccine (of rat tissue origin).

Results for prostate/seminal vesicle (PSV) weights (FIG. 7) are:
  Non-Vaccinated=1.90 gm (SD 1.11)
  MEM (Control) Vaccinated=2.87 gm (SD 2.00)
  GFT Tumor Vaccinated=0.38 (SD 0.499)

There was a significant difference observed between GFT Tumor Vaccinated and Media (Control) Vaccinated ($P<0.01$) PSV weights; and between GFT Tumor Vaccinated and Non-vaccinated ($P<0.05$) PSV weights.

Figure 8:
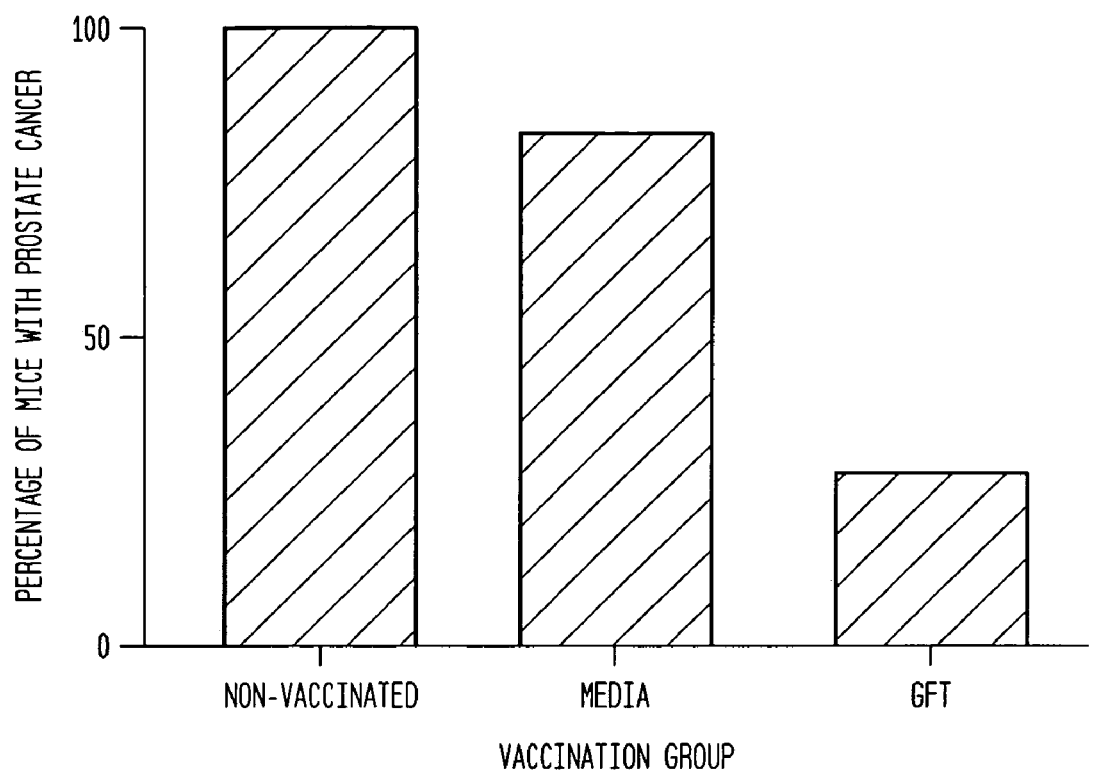

Histologic examination showed that PSV complexes weighing less than 0.84 gm did not demonstrate any evidence of tumor growth. Based on this, the incidence of animals with prostate tumors (FIG. 8) is:
  Non-Vaccinated=100% (7/7 animals)
  MEM (Control) Vaccinated=83.3% (5/6 animals)
  GFT Tumor Vaccinated=28.6% (2/7 animals)

Significantly fewer mice ($p\leq0.01$, Chi-square analysis with 2 degrees of freedom) administered human PC346 cells previously co-incubated with splenocytes from mice vaccinated with the GFT vaccine, had tumors at the time of necropsy, compared to mice administered human PC346 cells previously co-incubated with splenocytes from MEM (Control) vaccinated mice, or compared to the number of mice administered PC346 cells co-incubated with splenocytes from mice that had not been vaccinated at all (Non-Vaccinated). This shows that xenogeneic vaccination with the GFT vaccine stopped the development and progression of prostate cancer.

Activity against the human PC346 cells demonstrates efficacy of the vaccine against existing neoplastic cells, such as those in mature tumors, and also protection in a xenogeneic species (mouse) and against a xenogeneic cell line (human PC346 cells). This demonstrates evidence of homologous antigens between rat cancer cells and human cancer cells, and particularly homologous antigens between rat prostate tumor cells and human prostate cancer cells.

The GFT tissue vaccine and the PTE tissue vaccine prevent prostate cancer. Further, the vaccines can be used to target existing cancers. Vaccination with these preparations reduces the growth of primary transplanted tumors and of metastatic tumor foci. Following resection of the primary tumor, this trend persists with a significant reduction in the size of metastatic tumor foci. The tissue vaccines also have a striking efficacy as a xenogeneic cancer vaccine.

It is believed that xenogeneic vaccines allow the immune system to overcome tolerance to self-antigens expressed by tumors, thus stimulating a vigorous immunity to homologous antigens. In this way, xenogeneic vaccines have advantage over autologous or even allogeneic vaccines. The vaccine preparations are mixtures which contain a variety of potent antigens. In the case of prevention, the immune systems of vaccinated animals rapidly respond to preneoplastic lesions and effectively target occasional cancer cells as they develop. In the case of treatment, the immune system faces the much greater challenge of targeting an enormous number of active cells which can induce immune tolerance and quickly alter phenotype to adapt to selective pressures from treatment. The vaccines also include connective tissue components which are not neoplastic but which may be altered by cytokine or other signals from the neoplastic cells to organize needed connective tissue and stromal infrastructure for tumor support, growth, and progression. Because these connective tissue components are not neoplastic, they cannot alter their immunophenotype as easily as neoplastic cells in order to evade an immune response resulting from vaccination with a vaccine directed against these components. In this way, then, vaccination against tumor connective tissue and stromal components allows a protective immune response that the tumor cannot escape by rapidly altering immunophenotype, an escape mechanism commonly employed by neoplastic cells.

EXAMPLE 9

Hormone Responsive Tissue Associated Tumor and Cancers

The examples presented herein demonstrate that vaccines derived directly from animal tumor tissue can be used to prevent and treat prostate cancer. This approach can be generalized to other tumors, including breast, lung, testicular, uterine, and ovarian cancers. All of these cancers depend upon an extracellular connective tissue stroma to provide tumor infrastructure. One of the features of the tissue vaccines disclosed herein is that they include components derived from stroma and tumor tissue. The immunity provided by the present vaccine preparations to antigenic epitopes within the stroma is believed to contribute to the overall efficacy of the vaccine.

Many cancers, such as prostate cancer, cancers of the breast, uterus, ovary, and testicle, arise from a hormonally active tissue. All of these cancers are believed to be influenced to at least some degree by the hormonal status of the individual. This relationship suggests that similar mechanisms may be involved for these cancers with respect to tumor initiation and progression. The presently described tumor tissue vaccines against prostate cancer therefore have import in the development of vaccines for other cancers characteristic of other hormonally active tissues.

Prostate and breast cancer, and most forms of lung cancer, manifest as adenocarcinomas. These cancers thus arise from epithelium of glandular structures. Commonly, they are aggressive and metastatic. Aggressive forms of these cancers quickly become refractory to treatment. The similar origins and behaviors of these cancers suggest that they may have common mechanisms by which they arise and progress. For this reason, the presently described methods for vaccination to prevent and treat prostate cancer are also particularly relevant to the prevention and treatment of both lung and breast cancer.

EXAMPLE 10

GFT Tissue vs. PTE Tissue Vaccine

The present example is presented to demonstrate the utility of the present invention for providing anti-tumor vaccine preparations.

Two vaccines were evaluated. One of these vaccines was an extract (PTE) of cells harvested directly from in vivo tumors. The other vaccine was a preparation of glutaraldyhyde-processed tumor and connective tissue (GFT) cells.

In a model where splenocytes from vaccinated rats were incubated with rat live tumor cells prior to transplantation into homologous rats, PTE tissue vaccination resulted in an 80% reduction of subcutaneous tumors versus a 40% reduction resulting from GFT cell vaccination. In a long-term model where de novo prostate tumor formation was studied following vaccination, GFT tissue vaccination resulted in a 90% reduction in tumor formation versus a 50% reduction following PTE tissue vaccination.

The GFT-tissue vaccine logically contains a significant amount of antigens that would be expressed on the tumor cell surface. In contrast, the PTE-tissue vaccine contains antigens typically present in the tumor cytosol. While not intending to be limited to any particular theory or mechanism of action, the differences in antigen origin and composition between these two tissue vaccines may at least in part explain the differences observed in their activity against de novo tumor formation and subcutaneous tumor formation from transplanted mature tumor cells.

In the case of transplanted tumors, the immune response is directed against mature tumor cells which are being directly transplanted into the animal. These transplanted cells contained a mix of neoplastic cells, stroma, and connective tissue. As mature tumor cells, they actively release cytokines to further promote tumor progression and growth. The site of cytokine production is the cytosol. Thus, the PTE vaccine may contain a mixture of antigens which is more relevant to and efficient at protection against growth of mature tumor cells compared to the GFT cell vaccine as demonstrated in the transplantation model. However, both preparations provided significant anti-tumor activity.

The de novo model of autochthonous prostate tumor formation involves transformation of normal prostate epithelium into neoplastic tissue which eventually forms a tumor. As individual neoplastic cells arise, the most dominant antigens are cell surface antigens, since the cytosolic machinery of a small number of neoplastic cells is not able to produce and elaborate significant amounts of the cytokines needed for tumor maturation and progression. Because the immune response associated with the GFT tissue vaccine is associated primarily with cell surface antigens, the immune system is more efficient at halting these de novo preneoplastic lesions than the PTE tissue vaccine.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

BIBLIOGRAPHY

The following references are hereby specifically incorporated herein by reference.
1. Boring C C, et al. (1993), Cancer statistics. *CA Cancer J Clin,* 43:7-26.
2. Nomura Amy et al. (2000), *Cancer Epid Biomark Prev,* 9:883-87.
3. Brooks J D, et al. (2001), *J Urol* 2001; 166:2034-8.
4. Hursting S D, et al. (1990), *Prev Med,* 19:242-53.
5. Gann P H. (1999), *JAMA,;* 281:1682.
6. Gann P H, Ma J, Giovannucci E, et al. (1999), *Cancer Res.,* 59:1225-30.
7. Tjoa B A, et al. (1999), *Prostate;* 40:125-29.
8. Tjoa B A, Murphy GP. (2000), *Immunol Lett,* 74:87-93.
9. Gulley J, et al. (2002), *Prostate,* 53:109-17.
10. Pollard M, Luckert P H. (1975), *J Natl Cancer Inst,* 54:643-49.
11. Suckow M A, et al. (1991), *Lab Anim Sci.,* 41:151-56.
12. Ringler D H, Peter G K, Chrisp C E, et al. (1985), *Infect. Immun.,* 49:498-504.
13. Pollard M, Luckert P H. (1986), *J Natl Cancer Inst.,* 77:583-87.
14. Pollard M, Luckert P H. (1987), *Prostate,* 11:219-27.
15. Pollard M. (1998), *Prostate,* 37:1-4.
16. Hrouda D, et al. (1998), *Br J Urol.,* 82:870-76.
17. Hrouda D, et al. (2000), *Br J Urol Int,* 86:742-48.
18. Griffith T S, et al. (2001), *J Natl Cancer Inst,* 93:998-1007.
19. Charles L G, et al. (2000), *World J Urol,* 18:136-42.
20. Michael A, et al. (2005), *Clin Cancer Res,* 11:4469-78.
21. U.S. Pat. No. 6,406,689—Falkenberg et al.;
22. Wang et al. (1993), J. Clin. Invest., 91:684-692;
23. Shekhar et al. (2001), Cancer Res., 61:1320-1326.
24. Cunha et al. (2003), *Int. J. Cancer,* 107:1-10.
25. Yu-quan Wei (2002), *Anti-Cancer Drugs,* 13:229-235.
26. Fong et al. (2001), *J. Imm.,* 167: 7150-7156.
27. Srinivason et al. (2004), *J. Translational Med.,* 2:1-12.
28. Bergman et al. (2003), *Clin. Canc. Res.,* 9: 1284-1290.
29. Qui-ming He et al. (2003), *J. Biol. Chem.,* 278 (24): 21831-21886.
30. Fernandez-Acerno M J, et al. (2000), *Cancer* 88: 1544-48.
31. Ohashi Y, et al. (2000), *Anticancer Res.,* 20: 3025-30.
32. Furbert-Harris et al. (2003), *Prostate,* 57:165-175.

What is claimed is:

1. A tumor inhibiting composition comprising a tumor tissue preparation comprising:
   a heterologous mixture of stromal tissue and tumor tissue, and an adjuvant,
   wherein said tumor tissue preparation is exposed to a treatment which preserves tumor antigenic species characteristic of the tumor and stromal tissue.

2. The tumor inhibiting composition of claim 1, wherein the heterologous mixture of stromal tissue and tumor tissue is treated with glutaraldehyde.

3. The tumor inhibiting composition of claim 1, wherein the heterologous mixture of stromal tissue and tumor tissue is treated with potassium thiocyanate.

4. The tumor inhibiting composition of claim 1, comprising a 50:50 mixture of the whole tumor tissue preparation and the adjuvant.

5. The tumor inhibiting composition of claim 1, further comprising other non-tumor tissue.

6. The tumor inhibiting composition of claim 1, wherein the stromal tissue comprises non-human stromal tissue.

7. The tumor inhibiting composition of claim 1, comprising a pharmaceutically acceptable preparation.

8. The tumor inhibiting composition of claim 1, comprising a xenogeneic cancer preparation.

9. The tumor inhibiting composition of claim 1, comprising a human tumor tissue preparation.

10. The tumor inhibiting composition of claim 1 wherein the composition is suitable for parenteral administration.

11. The tumor inhibiting composition of claim 10 wherein the composition is suitable for subcutaneous parenteral administration.

12. The tumor inhibiting composition of claim 1 wherein the composition is a non-human tissue cancer preparation.

13. The tumor inhibiting composition of claim 1 wherein the composition is a human tissue cancer preparation.

14. A composition comprising a tumor tissue preparation comprising:
a heterologous cellular mixture of stromal tissue and prostate tumor tissue, and an adjuvant,
said tumor tissue preparation inhibiting tumor cell proliferation.

15. The composition of claim 14, comprising a 50:50 mixture of the tumor tissue preparation and the adjuvant.

16. The composition of claim 14, further comprising other non-tumor tissue.

17. The composition of claim 14, wherein the stromal tissue comprises non-human stromal tissue.

18. The composition of claim 14, comprising a pharmaceutically acceptable preparation.

19. The composition of claim 14, comprising a xenogeneic cancer preparation.

20. The composition of claim 14, comprising a human whole tumor tissue preparation.

21. The composition of claim 14 wherein the preparation is suitable for parenteral administration.

22. The composition of claim 11 wherein the preparation is suitable for subcutaneous parenteral administration 23. The composition of claim 14 wherein the preparation is a non-human tissue cancer preparation.

24. The composition of claim 23 wherein the preparation is a human tissue cancer preparation.

25. A method of treatment for inhibiting tumor growth, said method comprising:
a first treatment with an effective amount of a tumor tissue preparation of claim; and
a subsequent treatment with an effective amount of the whole tumor tissue preparation of claim 1, wherein tumor growth is inhibited.

26. The method of claim 23, wherein the tumor tissue preparation of the first treatment is glutaraldehyde processed.

27. The method of claim 17, wherein the subsequent treatment is administered about 7 days after the first treatment.

28. A method of inhibiting tumor growth, said method comprising:
administering an effective amount of the preparation of claim 1 to an animal; and
inhibiting de novo tumor growth.

29. The method of claim 28, wherein the animal is a human.

30. The method of claim 28, wherein the preparation is glutaraldehyde processed.

31. The method of claim 28, wherein the tumor tissue comprises prostate tissue.

32. The method of claim 28, wherein the whole tumor tissue preparation comprises a 50:50 mixture of the tumor tissue preparation and the adjuvant.

33. The method of claim 28, wherein the whole tumor tissue preparation comprises a xenogeneic cancer preparation.

34. The method of claim 28, wherein the preparation is a human tissue cancer preparation.

35. The method of claim 28, wherein the preparation is a pharmaceutically acceptable preparation.

36. A method of preparing a tumor tissue preparation capable of preventing tumor growth and occurrence comprising:
providing a tumor tissue preparation comprising a heterologous mixture of tumor tissue and connective tissue; and
exposing the tumor tissue preparation to a treatment comprising glutaraldehyde, wherein said whole tumor tissue preparation is capable of inhibiting tumor growth.

37. The method of claim 36, wherein the treatment comprises an incubation of the whole tumor tissue preparation in about 2.5% glutaraldehyde (v/v) at about 37° C. for about 120 minutes.

38. A method of preparing a composition comprising a tumor tissue preparation, the method comprising:
providing a tumor tissue preparation comprising a heterologous mixture of tumor tissue and connective tissue; and
exposing the tumor tissue preparation to a treatment comprising potassium thiocyanate, wherein said whole tumor tissue preparation is capable of inhibiting tumor growth.

39. The method of claim 38, wherein the tumor tissue preparation comprises a tissue suspension.

40. A method of preparing a tumor tissue preparation capable of inhibiting prostate tumor growth comprising:
preparing a tumor tissue preparation, said tumor tissue preparation comprising a heterologous mixture of stromal tissue and prostate tumor tissue, wherein the prostate tumor tissue is derived from tumor tissue of a xenogeneic species; and
exposing the tumor tissue preparation to a treatment which preserves tumor antigenic species characteristic of the tumor and stromal tissue.

41. The method of claim 40, wherein the xenogeneic species is non-human.

* * * * *

UNITED STATES PATENT AND TRADEMARK OFFICE
CERTIFICATE OF CORRECTION

| | | |
|---|---|---|
| PATENT NO. | : 8,257,715 B1 | Page 1 of 1 |
| APPLICATION NO. | : 11/209766 | |
| DATED | : September 4, 2012 | |
| INVENTOR(S) | : Mark A. Suckow et al. | |

It is certified that error appears in the above-identified patent and that said Letters Patent is hereby corrected as shown below:

<u>Claim 25</u>

Line 54, delete "whole tumor tissue".

<u>Claim 32</u>

Line 6, delete "whole tumor tissue".

Signed and Sealed this
Twenty-ninth Day of January, 2013

David J. Kappos
*Director of the United States Patent and Trademark Office*

UNITED STATES PATENT AND TRADEMARK OFFICE
CERTIFICATE OF CORRECTION

PATENT NO. : 8,257,715 B1
APPLICATION NO. : 11/209766
DATED : September 4, 2012
INVENTOR(S) : Mark A. Suckow et al.

Page 1 of 1

It is certified that error appears in the above-identified patent and that said Letters Patent is hereby corrected as shown below:

Column 15, line 54 (Claim 25, line 6), delete "whole tumor tissue".

Column 16, lines 11-12 (Claim 32, lines 1-2), delete "whole tumor tissue".

This certificate supersedes the Certificate of Correction issued January 29, 2013.

Signed and Sealed this
Nineteenth Day of February, 2013

Teresa Stanek Rea
*Acting Director of the United States Patent and Trademark Office*